US008658846B2

(12) United States Patent
Knapp

(10) Patent No.: US 8,658,846 B2
(45) Date of Patent: *Feb. 25, 2014

(54) PROCESSES FOR SEPARATION OF 2,3,3,3-TETRAFLUOROPROPENE FROM HYDROGEN FLUORIDE BY AZEOTROPIC DISTILLATION

(75) Inventor: Jeffrey P. Knapp, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 447 days.

This patent is subject to a terminal disclaimer.

(21) Appl. No.: 12/918,137

(22) PCT Filed: Feb. 19, 2009

(86) PCT No.: PCT/US2009/034470
§ 371 (c)(1),
(2), (4) Date: Aug. 18, 2010

(87) PCT Pub. No.: WO2009/105521
PCT Pub. Date: Aug. 27, 2009

(65) Prior Publication Data
US 2012/0261252 A1    Oct. 18, 2012

Related U.S. Application Data

(60) Provisional application No. 61/030,371, filed on Feb. 21, 2008.

(51) Int. Cl.
*B01D 3/36* (2006.01)
*C07C 17/383* (2006.01)
*C07C 17/386* (2006.01)

(52) U.S. Cl.
USPC ................ 570/178; 203/67; 203/68; 203/75; 203/77; 423/488

(58) Field of Classification Search
USPC ......... 203/2, 3, 52, 56, 62, 63, 67, 68, 75, 77; 570/178; 423/488
See application file for complete search history.

(56) References Cited

U.S. PATENT DOCUMENTS

| | | | |
|---|---|---|---|
| 2,831,902 A | 4/1958 | Hamilton et al. | |
| 2,931,840 A | 4/1960 | Marquis | |
| 2,996,555 A | 8/1961 | Rausch | |
| 3,271,273 A * | 9/1966 | Fox et al. | 203/12 |
| 4,978,649 A | 12/1990 | Surovikin et al. | |

(Continued)

FOREIGN PATENT DOCUMENTS

| | | |
|---|---|---|
| EP | 0940382 B1 | 9/1999 |
| WO | 9920585 | 4/1999 |

(Continued)

OTHER PUBLICATIONS

Jeanneaux et al., "Addition Thermique Des IODO-1-Perfluoroalcanes Sur Les Perfluoroalkylethylenes", Journal of Fluorine Chemistry, 4, (1974), pp. 261-270.

(Continued)

*Primary Examiner* — Virginia Manoharan

(57) ABSTRACT

Disclosed herein are processes for separation of 2,3,3,3-tetrafluoropropene and hydrogen fluoride using azeotropic distillation. Additionally, disclosed are processes for separating mixtures of 2,3,3,3-tetrafluoropropene, hydrogen fluoride and 1,1,1,2,3-pentafluoropropane (HFC-245eb) and/or 1,1,1,2,2-pentafluoropropane (HFC-245cb) by azeotropic distillation.

16 Claims, 8 Drawing Sheets

(56) References Cited

U.S. PATENT DOCUMENTS

| | | | |
|---|---|---|---|
| 5,396,000 | A | 3/1995 | Nappa et al. |
| 5,679,875 | A | 10/1997 | Aoyama et al. |
| 6,031,141 | A | 2/2000 | Mallikarjuna et al. |
| 6,184,426 | B1 | 2/2001 | Belen'Kill et al. |
| 6,303,838 | B1 | 10/2001 | Boehmer et al. |
| 6,369,284 | B1 | 4/2002 | Nappa et al. |
| 7,189,884 | B2 | 3/2007 | Mukhopadhyay et al. |
| 8,273,928 | B2 * | 9/2012 | Knapp et al. ............... 570/136 |
| 2002/0143215 | A1 * | 10/2002 | Tung et al. ................. 570/161 |
| 2003/0028057 | A1 | 2/2003 | Owens et al. |
| 2006/0106263 | A1 | 5/2006 | Miller et al. |
| 2006/0116538 | A1 | 6/2006 | Miller et al. |
| 2007/0099811 | A1 | 5/2007 | Miller et al. |
| 2007/0100173 | A1 | 5/2007 | Miller et al. |
| 2007/0100174 | A1 | 5/2007 | Miller et al. |
| 2007/0100175 | A1 | 5/2007 | Miller et al. |
| 2007/0100176 | A1 | 5/2007 | Miller et al. |
| 2008/0051612 | A1 | 2/2008 | Knapp et al. |

FOREIGN PATENT DOCUMENTS

| | | |
|---|---|---|
| WO | 9926907 | 6/1999 |
| WO | 9926908 | 6/1999 |
| WO | 2008008519 A1 | 1/2008 |
| WO | 2009105517 | 8/2009 |
| WO | 2009105521 | 8/2009 |

OTHER PUBLICATIONS

PCT International Search Report for International Application No. PCT/US2009/034470 dated Feb. 19, 2009.

* cited by examiner

PROCESSES FOR SEPARATION OF 2,3,3,3-TETRAFLUOROPROPENE FROM HYDROGEN FLUORIDE BY AZEOTROPIC DISTILLATION

BACKGROUND INFORMATION

1. Field of the Disclosure

This disclosure relates in general to processes for separating HF from fluoroolefins. In particular, the disclosure relates to processes for separating HF from 2,3,3,3-tetrafluoropropene by azeotropic distillation.

This application is a national stage entry of PCT/US2009/034470, with an international filing date of Feb. 19, 2009.

2. Description of the Related Art

The chemical manufacture of fluoroolefins may produce mixtures of the desired fluoroolefins and hydrogen fluoride (HF). The separation of fluoroolefins and HF is not always easily accomplished. Existing methods of distillation and decantation are very often ineffective for separation of these compounds. Aqueous scrubbing may be effective, but requires the use of large amounts of scrubbing solutions and produces excessive waste as well as wet product that must then be dried. Therefore, there is a need for new methods of separating HF from fluoroolefins.

SUMMARY

In one embodiment is provided a process for separating a mixture comprising HF and HFC-1234yf, said process comprising: a) feeding the composition comprising HF and HFC-1234yf to a first distillation column; b) removing an azeotrope composition comprising HF and HFC-1234yf as a first distillate and either i) HF or ii) HFC-1234yf as a first column bottoms composition; c) condensing the first distillate to form 2 liquid phases, being i) an HF-rich phase and ii) an HFC-1234yf-rich phase; and d) recycling a first liquid phase enriched in the same compound that is removed as the first column bottoms, said first liquid phase being either i) HF-rich phase or ii) HFC-1234yf-rich phase, back to the first distillation column.

In another embodiment is provided a process for separating HFC-1234yf from a mixture comprising hydrogen fluoride and said HFC-1234yf, wherein said HFC-1234yf is present in a concentration greater than the azeotrope concentration of hydrogen fluoride and said HFC-1234yf, said process comprising a) feeding said mixture comprising hydrogen fluoride and said HFC-1234yf to a first distillation column; b) removing an azeotrope composition comprising hydrogen fluoride and HFC-1234yf as a first distillate from the first distillation column; c) recovering HFC-1234yf essentially free of hydrogen fluoride from the bottom of the first distillation column; d) condensing the azeotrope composition to form two liquid phases, being i) a hydrogen fluoride-rich phase and ii) an HFC-1234yf-rich phase; and e) recycling the HFC-1234yf-rich phase to the first distillation column.

In another embodiment is provided a process for separating hydrogen fluoride from a mixture comprising hydrogen fluoride and HFC-1234yf, wherein hydrogen fluoride is present in a concentration greater than the azeotrope concentration for hydrogen fluoride and said HFC-1234yf, said process comprising a) feeding said mixture comprising hydrogen fluoride and HFC-1234yf to a first distillation column; b) removing an azeotrope or azeotrope-like composition comprising HFC-1234yf and HF as a distillate from the first distillation column; c) recovering hydrogen fluoride essentially free of HFC-1234yf from the bottom of the first distillation column; d) condensing the azeotrope composition to form two liquid phases, being an HFC-1234yf-rich phase and a hydrogen fluoride-rich phase; and e) recycling the HF-rich phase to the first distillation column.

In another embodiment is provided a process for the purification of HFC-1234yf from a mixture comprising HFC-1234yf and HF, wherein said HFC-1234yf is present in said mixture in a concentration greater than the azeotrope concentration for said HFC-1234yf and HF, said process comprising a) adding an entrainer to the mixture comprising HFC-1234yf and HF thus forming a second mixture; b) distilling said second mixture in a first distillation step to form a first distillate composition comprising HF, HFC-1234yf, and entrainer, and a first bottoms composition comprising HFC-1234yf; c) condensing said first distillate composition to form two liquid phases, being i) an HF-rich phase and ii) an entrainer-rich phase; and d) optionally recycling the entrainer-rich phase back to the first distillation step.

In another embodiment is provided a process for the purification of HF from a mixture comprising HFC-1234yf and HF, wherein HF is present in a concentration greater than the azeotrope concentration for HF and said HFC-1234yf, said process comprising a) adding an entrainer to the mixture comprising HFC-1234yf and HF thus forming a second mixture; b) distilling said second mixture in a first distillation step to form a first distillate composition comprising an HF, entrainer, and HFC-1234yf, and a first bottoms composition comprising HF; c) condensing said first distillate composition to form two liquid phases, being i) an entrainer-rich phase and ii) an HF-rich phase; and d) optionally recycling the HF-rich phase back to the first distillation step.

In another embodiment is provided a process for the separation of HFC-1234yf from a mixture of HFC-1234yf, HF, and at least one of HFC-245cb or HFC-245eb, said process comprising a) subjecting said mixture to a first distillation step, wherein additional HFC-1234yf is fed from a second distillation step, to form a first distillate comprising an azeotrope of HFC-1234yf and HF and a first bottoms composition comprising at least one of HFC-245cb or HFC-245eb; b) feeding said first distillate to a second distillation step to form a second distillate comprising an azeotrope of HFC-1234yf and HF and a second bottoms composition comprising HFC-1234yf essentially free of HF; c) condensing said second distillate to form two liquid phases, being i) an HF-rich phase and ii) an HFC-1234yf-rich phase; and d) recycling the HFC-1234yf-rich phase from (c) back to the first distillation step.

In another embodiment is provided a process for separating HF from a mixture comprising HFC-1234yf, HF, and at least one of HFC-245cb or HFC-245eb, said process comprising a) adding an entrainer to the mixture comprising HFC-1234yf, HF, and at least one of HFC-245cb or HFC-245eb thus forming a second mixture; b) distilling said second mixture in a first distillation step to form a first distillate composition comprising HF and entrainer and a first bottoms composition comprising HFC-1234yf and at least one of HFC-245cb or HFC-245eb; c) condensing said first distillate composition to form two liquid phases, being (i) an entrainer-rich phase and (ii) an HF-rich phase; and d) recycling the entrainer-rich phase back to the first distillation step.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
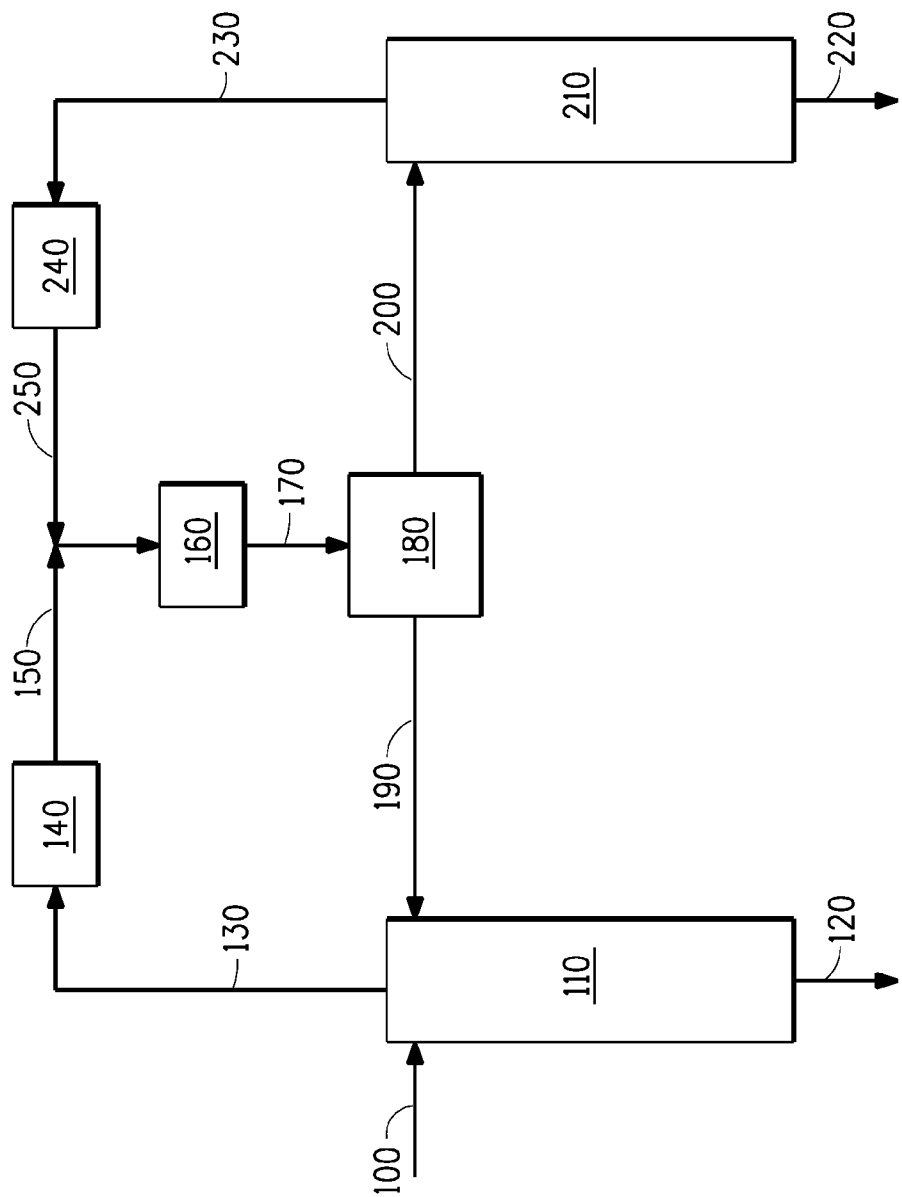
FIG. 1 is an illustration of one embodiment of an azeotropic distillation for the separation of HF and HFC-1234yf with no added entrainer.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims.

1. Definitions and Clarification of Terms

Before addressing details of embodiments described below, some terms are defined or clarified.

By azeotropic or azeotrope composition is meant a constant-boiling mixture of two or more substances that boils at a constant composition and thus behaves as a single substance. Constant-boiling compositions are characterized as azeotropic because they exhibit either a maximum or minimum boiling point, when compared with the boiling points of the individual components. Azeotropic compositions are also characterized by a minimum or a maximum in the vapor pressure measurements relative to the vapor pressure of the neat components in a PTx cell as a function of composition at a constant temperature. For homogeneous azeotropes, where the vapor phase is in equilibrium with a single liquid phase, the compositions of the vapor and liquid phases are identical. However, for heterogeneous azeotropes, where the vapor phase is in equilibrium with two liquid phases, all three equilibrium phases can have different, but constant, compositions.

As used herein, the term "azeotrope-like composition" (also commonly referred to as a "near azeotropic composition") means a constant boiling, or substantially constant boiling liquid admixture of two or more substances that behaves as a single substance. One way to characterize an azeotrope-like composition is that the composition of the vapor produced by partial evaporation or distillation of the liquid does not change substantially throughout the partial evaporation or distillation. Similarly, the composition of the liquid phase or phases present does not change substantially during the partial evaporation or distillation. That is, the admixture boils/distills/refluxes without substantial composition change. This is to be contrasted with non-azeotrope-like compositions in which the liquid composition changes to a substantial degree during boiling or evaporation. Another way to characterize an azeotrope-like composition is that the bubble point vapor pressure of the composition and the dew point vapor pressure of the composition at a particular temperature are substantially the same. Herein, a composition is considered to be azeotrope-like if the difference in dew point pressure and bubble point pressure is less than or equal to 3 percent (based upon the bubble point pressure).

By high-boiling azeotrope is meant that an azeotropic or azeotrope-like composition boils at a higher temperature at any given pressure than any one of the compounds that comprise it would separately boil at that pressure. Alternately, by high-boiling azeotrope is meant any azeotropic or azeotrope-like composition that has a lower vapor pressure at any given temperature than any one of the compounds that comprise it would separately have at that temperature.

By low-boiling-azeotrope is meant that an azeotropic or azeotrope-like composition boils at a lower temperature at any given pressure than any one of the compounds that comprise it would separately boil at that pressure. Alternately, by low-boiling azeotrope is meant any azeotropic or azeotrope-like composition that has a higher vapor pressure at any given temperature than the vapor pressure of any one of the compounds that comprise the azeotrope would separately have at that temperature.

It is possible to characterize an azeotropic or azeotrope-like composition as a substantially constant-boiling admixture that may appear under many guises, depending upon the conditions chosen, by several criteria:

The composition can be defined as an azeotrope of two compounds because the term "azeotrope" is at once both definitive and limitative, and requires effective amounts of those two or more compounds for this unique composition of matter which can be a constant-boiling composition.

It is well known by those skilled in the art, that, at different pressures, the composition of a given azeotrope or azeotrope-like composition will vary at least to some degree, as will the boiling point temperature. Thus, an azeotropic or azeotrope-like composition of two compounds represents a unique type of relationship but with a variable composition which depends on temperature and/or pressure. Therefore, compositional ranges, rather than fixed compositions, are often used to define azeotropes and azeotrope-like compositions.

An azeotrope or azeotrope-like composition of two compounds can be characterized by defining compositions characterized by a boiling point at a given pressure, thus giving identifying characteristics without unduly limiting the scope of the invention by a specific numerical composition, which is limited by and is only accurate as the analytical equipment available.

It is recognized in the art that both the boiling point and the weight (or mole) percentages of each component of the azeotropic composition may change when the azeotrope or azeotrope-like liquid composition is allowed to boil at different pressures. Thus, an azeotropic or an azeotrope-like composition may be defined in terms of the unique relationship that exists among components or in terms of the exact weight (or mole) percentages of each component of the composition characterized by a fixed boiling point at a specific pressure.

As used herein, the term "azeotrope" is meant to refer to azeotrope compositions and/or azeotrope-like compositions.

By entrainer is meant any compound that, when added to a first mixture, forms one or more azeotropes with the components of the mixture to facilitate separation of the components of the mixture. As used herein, the terms "entrainer" and "entraining agent" are used interchangeably and are to be interpreted as having identical meaning.

By azeotropic distillation is meant a process in which a distillation column is operated under conditions to cause one or more azeotropic or azeotrope-like composition to form, and thereby facilitates the separation of the components of the mixture. Azeotropic distillations may occur where only the components of the mixture to be separated are distilled, or where an entrainer is added that forms an azeotrope with one or more of the components of the initial mixture. Entrainers that act in this manner, that is to say, that form an azeotrope with one of more of the components of the mixture to be separated thus facilitating the separation of those components by distillation, are more commonly called azeotroping agents or azeotropic entrainers.

In conventional or azeotropic distillations, the overhead or distillate stream exiting the column may be condensed using conventional reflux condensers. At least a portion of this condensed stream can be returned to the top of the column as reflux, and the remainder recovered as product or for optional processing. The ratio of the condensed material which is returned to the top of the column as reflux to the material removed as distillate is commonly referred to as the reflux ratio. The compounds and entrainer exiting the column as distillate or distillation bottoms stream can then be passed to a stripper or second distillation column for separation by using conventional distillation, or may be separated by other methods, such as decantation. If desired, the entrainer may then be recycled back to the first distillation column for reuse.

The specific conditions which can be used for practicing the invention depend upon a number of parameters, such as the diameter of the distillation column, feed points, number of separation stages in the column, among others. In one embodiment, the operating pressure of the distillation system may range from about 5 to 500 psia, in another embodiment, about 20 to 400 psia. Normally, increasing the reflux ratio results in increased distillate stream purity, but generally the reflux ratio ranges between 1/1 to 200/1. The temperature of the condenser, which is located adjacent to the top of the column, is normally sufficient to substantially fully condense the distillate that is exiting from the top of the column, or is that temperature required to achieve the desired reflux ratio by partial condensation.

The problems associated with conventional distillation may be solved by a distillation process using an entrainer. The difficulty in applying this method is that there is no known way, short of experimentation, of predicting which if any compound will be an effective entrainer.

Hydrogen fluoride (HF, anhydrous) is a commercially available chemical or can be produced by methods known in the art.

2,3,3,3-tetrafluoropropene (HFC-1234yf, $CF_3CF=CH_2$) may be prepared by known methods, such as dehydrofluorination of 1,1,1,2,2-pentafluoropropane (HFC-245cb, $CF_3CF_2CH_3$) or 1,1,1,2,3-pentafluoropropane (HFC-245eb, $CF_3CHFCH_2F$). HFC-245cb may be prepared by processes described in the art such as for instance in U.S. Pat. No. 6,184,426. HFC-245eb may be prepared by processes described in the art such as for instance in U.S. Pat. No. 5,396,000.

U.S. Patent Publication no. 2007-0100175 A1 discloses the azeotrope and azeotrope-like (also known as near-azeotrope) compositions for HFC-1234yf and HF. These azeotrope and azeotrope-like compositions may be used in processes for separating HFC-1234yf from a mixture comprising HF and HFC-1234yf. Additionally, the azeotropic compositions as described therein may be used in similar methods for separation or purification of HFC-1234yf from mixtures comprising HFC-1234yf, HF and at least one of HFC-245cb or HFC-245eb.

The term "entrainer" is used herein to describe any compound that would be effective in separation of fluoroolefins from mixtures comprising HF and fluoroolefin in an azeotropic distillation process. Included as useful entrainers are those compounds that form azeotropes with one or more of the components of a mixture, including fluoroolefins, HF, and possible hydrofluorocarbons for which the boiling point of at least one of such azeotropes is lower than the boiling point of the fluoroolefin/HF azeotrope.

Entrainers may be selected from the group consisting of hydrocarbons, chlorocarbons, chlorofluorocarbons, hydrochlorofluorocarbons, hydrofluorocarbons, perfluorocarbons, fluoroethers, HFPO, $SF_6$, chlorine, hexafluoroacetone, and mixtures thereof.

Hydrocarbon entrainers comprise compounds containing 1 to 5 carbon atoms and hydrogen. Hydrocarbon entrainers may be linear, branched, cyclic, saturated or unsaturated compounds. Representative hydrocarbon entrainers include but are not limited to methane, ethane, ethylene, acetylene, vinylacetylene, n-propane, propylene, propyne, cyclopropane, cyclopropene, propadiene, n-butane, isobutane, 1-butene, isobutene, 1,3-butadiene, 2,2-dimethylpropane, cis-2-butene, trans-2-butene, 1-butyne, n-pentane, isopentane, neopentane, cyclopentane, 1-pentene, 2-pentene, and mixtures thereof.

Chlorocarbon entrainers comprise compounds containing carbon, chlorine and optionally hydrogen, including but not limited to methylene chloride ($CH_2Cl_2$), and methyl chloride ($CH_3Cl$).

Chlorofluorocarbon (CFC) entrainers comprise compounds with carbon, chlorine and fluorine. Representative CFCs include but are not limited to dichlorodifluoromethane (CFC-12), 2-chloro-1,1,2-trifluoroethylene, chloropentafluoroethane (CFC-115), 1,2-dichloro-1,1,2,2-tetrafluoroethane (CFC-114), 1,1-dichloro-1,2,2,2-tetrafluoroethane (CFC-114a), 1,1,2-trichloro-1,2,2-trifluoroethane (CFC-113), 1,1,1-trichloro-2,2,2-trifluoroethane (CFC-113a), 1,1, 2-trichloro-1,2,3,3,3-pentafluoropropane (CFC-215bb), 2,2-dichloro-1,1,1,3,3,3-hexafluoropropane (CFC-216aa), 1,2-dichloro-1,1,2,3,3,3-hexafluoropropane (CFC-216ba), 2-chloro-1,1,1,2,3,3,3-heptafluoropropane (CFC-217ba), 2-chloro-1,1,3,3,3-pentafluoropropene (CFC-1215xc), and mixtures thereof.

Hydrochlorofluorocarbon (HCFC) entrainers comprise compounds with carbon, chlorine, fluorine and hydrogen. Representative HCFCs include but are not limited to dichlorofluoromethane (HCFC-21), 1,1-dichloro-3,3,3-trifluoroethane (HCFC-123), 1,1-dichloro-1-fluoroethane (HCFC-141b), 2-chloro-1,1,1,2-tetrafluoroethane (HCFC-124), 1-chloro-1,1,2,2-tetrafluoroethane (HCFC-124a), 2-chloro-1,1,1-trifluoroethane (HCFC-133a), 1-chloro-1,1-difluoroethane (HCFC-142b), 2-chloro-1,1-difluoroethylene (HCFC-1122), and mixtures thereof.

Hydrofluorocarbon (HFC) entrainers comprise compounds that contain carbon, hydrogen and fluorine. Representative HFCs include but are not limited to 1,1,2-trifluoroethylene (HFC-1123), 1,1-difluoroethylene (HFC-1132a), 2,3,3,3-tetrafluoropropene (HFC-1234yf), and mixtures thereof.

Perfluorocarbon (PFC) entrainers comprise compounds with carbon and fluorine only. Representative PFCs include but are not limited to hexafluoroethane (PFC-116), octafluoropropane (PFC-218), 1,1,1,4,4,4-hexafluoro-2-butyne (PFBY-2), hexafluoropropylene (HFP, PFC-1216), hexafluorocyclopropane (PFC-C216), octafluorocyclobutane (PFC-C318), decafluorobutane (PFC-31-10, any isomer(s)), 2,3-dichloro-1,1,1,4,4,4-hexafluoro-2-butene (PFC-1316mxx), octafluoro-2-butene (PFC-1318my, cis and trans), hexafluorobutadiene (PFC-2316), and mixtures thereof.

Fluoroether entrainers comprise compounds with carbon, fluorine, optionally hydrogen and at least one ether group oxygen. Representative fluoroethers include but are not limited to trifluoromethyl-difluoromethyl ether ($CF_3OCHF_2$, HFOC-125E), 1,1-difluorodimethyl ether, tetrafluorodimethylether (HFOC-134E), difluoromethyl methyl ether ($CHF_2OCH_3$, HFOC-152aE), pentafluoroethyl methyl ether, and mixtures thereof.

Miscellaneous other compounds that may be useful as entrainers include HFPO, chlorine ($Cl_2$), hexafluoroacetone, PMVE (perfluoromethylvinylether), PEVE (perfluoroethylvinylether), and mixtures thereof.

Entrainers as described above are available commercially or may be produced by methods known in the art.

As used herein, by "essentially free of" is meant that a composition contains less than about 100 ppm (mole basis), less than about 10 ppm or less than about 1 ppm, of the specified component. If a composition is essentially free of more than one component, then the total concentration of those components is less than about 100 ppm, less than about 10 ppm, or less than about 1 ppm.

The process equipment for all the processes disclosed herein and the associated feed lines, effluent lines and associated units may be constructed of materials resistant to hydrogen fluoride. Typical materials of construction, well-known to the art, include stainless steels, in particular of the austenitic type, and the well-known high nickel alloys such as Monel® nickel-copper alloys, Hastelloy® nickel based alloys and Inconel® nickel-chromium alloys.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

2. Separation Process—Azeotropic Distillation with No Entrainer

It has been discovered that some fluoroolefins form azeotrope compositions with HF. Generally, the fluoroolefin/HF azeotrope composition will boil at a lower temperature than either of the corresponding pure compounds. Several examples of such fluoroolefin/HF azeotropes are disclosed in U.S. Patent Publication numbers 2007-0100173 A1, 2007-0100174 A1, 2007-0099811 A1, 2007-0100175 A1, 2007-0100176 A1, and 2006-0116538 A1.

It has been unexpectedly determined that in a few cases azeotrope compositions comprising fluoroolefins and HF may form two liquid phases when condensed and/or cooled. For HFC-1234yf, the two phases comprise an HFC-1234yf-rich phase and an HF-rich phase. This phase behavior allows unique separation schemes utilizing liquid-liquid separation (such as decantation) of the two phases that are not possible with many saturated hydrofluorocarbons, which in general do not phase separate in the same manner.

In one embodiment, the present disclosure provides a process for separating a mixture comprising HF and HFC-1234yf, said process comprising a) feeding the composition comprising HF and HFC-1234yf to a first distillation column; b) removing an azeotrope composition comprising HF and HFC-1234yf as a first distillate and either i) HF or ii) HFC-1234yf as a first column bottoms composition; c) condensing the first distillate to form two liquid phases, being i) an HF-rich phase and ii) an HFC-1234yf-rich phase; and d) recycling a first liquid phase enriched in the same compound that is removed as the first column bottoms, said first liquid phase being either i) HF-rich phase or ii) HFC-1234yf-rich phase, back to the first distillation column.

Additionally, in another embodiment, the process as described in the paragraph above may further comprise feeding a second liquid phase not recycled in step (d), said second liquid phase being either i) HF-rich phase or ii) HFC-1234yf-rich phase, to a second distillation zone, and recovering the compound not recovered in step (b) as the first column bottoms composition as the second column bottoms composition.

In another embodiment, a process is provided for separating HFC-1234yf from a mixture comprising hydrogen fluoride and said HFC-1234yf, wherein said HFC-1234yf is present in a concentration greater than the azeotrope concentration for hydrogen fluoride and said HFC-1234yf, said process comprising: a) feeding said mixture comprising hydrogen fluoride and said HFC-1234yf to a first distillation column; b) removing an azeotrope composition comprising hydrogen fluoride and HFC-1234yf as a first distillate from the first distillation column; c) recovering HFC-1234yf essentially free of hydrogen fluoride as a first bottoms composition from the first distillation column; and
d) condensing the first distillate to form two liquid phases, being i) a hydrogen fluoride-rich phase and ii) an HFC-1234yf-rich phase; and e) recycling the HFC-1234yf-rich phase to the first distillation column.

In another embodiment, the process may further comprise: a) feeding the hydrogen fluoride-rich phase to a second distillation column, and b) recovering hydrogen fluoride essentially free of HFC-1234yf from the bottom of the second distillation column.

In another embodiment, the second distillate comprising HF and HFC-1234yf may be recycled to the two liquid phases.

In one embodiment, wherein the composition comprising HF and HFC-1234yf has a concentration of HFC-1234yf that is greater than the azeotrope concentration for HFC-1234yf and HF, the first distillation column removes the excess HFC-1234yf from the bottom of the column and the azeotrope composition exits the top of the column as the distillate. In another embodiment, the azeotrope composition comprising HF and HFC-1234yf may be condensed and cooled thereby forming two liquid phases, an HF-rich phase and an HFC-1234yf-rich phase.

In one embodiment, the HFC-1234yf-rich phase is recycled back to the first distillation column and the HF-rich phase is fed to a second distillation column. As the HF-rich phase may have HF in excess of the azeotrope composition for HF/HFC-1234yf, the excess HF will be removed from the second distillation column bottom.

Referring now to FIG. 1, one embodiment of this process is illustrated. A composition comprising HF and HFC-1234yf is fed to a first column 110 via stream 100. This first column is operated under appropriate conditions to approach the low-boiling HF/HFC-1234yf azeotrope. Because HFC-1234yf is being fed to this first column in excess of that needed to form the azeotrope with the HF, HFC-1234yf is recovered as the bottoms of the column via stream 120, while a composition near to the HF/HFC-1234yf azeotrope is recovered as distillate via stream 130. Stream 130 is condensed in 140, mixed with a nearly azeotropic composition recycled from a second column 210 via stream 250 and the combined stream is sub-cooled in cooler 160 and sent to decanter 180 where the combined stream 170 separates into an HFC-1234yf-rich stream 190 and an HF-rich stream 200. Stream 190 is recycled to the first column as reflux. Stream 200 is fed to the top stage of the second distillation column 210, operated under conditions to approach the HF/HFC-1234yf azeotrope. Because the HF is being fed to this second column in excess of that needed to form the low-boiling HF/HFC-1234yf azeotrope, HF is recovered as the bottoms of the column via stream 220 while a composition close to the HF/HFC-1234yf azeotrope is recovered as distillate via stream 230. Stream 230 is condensed in 240, mixed with the nearly azeotropic composition from the first column via stream 150 and fed to cooler 160 and then decanter 180.

In another embodiment, a process is provided for separating hydrogen fluoride from a mixture comprising hydrogen fluoride and HFC-1234yf, wherein hydrogen fluoride is present in a concentration greater than the azeotrope concentration for hydrogen fluoride and said HFC-1234yf, said process comprising: a) feeding said mixture comprising hydrogen fluoride and HFC-1234yf to a first distillation column; b) removing an azeotrope composition comprising HFC-1234yf and HF as a first distillate from the first distillation column; c) recovering hydrogen fluoride essentially free of HFC-1234yf from the bottom of the first distillation column; d) condensing the first distillate to form two liquid phases, being an HFC-1234yf-rich phase and a hydrogen fluoride-rich phase; and e) recycling the HF-rich phase to the first distillation column.

In another embodiment, the process may further comprise: a) feeding the HFC-1234yf-rich phase to a second distillation column; and b) recovering HFC-1234yf essentially free of hydrogen fluoride from the bottom of the second distillation column.

In another embodiment, the process may further comprise: recycling the hydrogen fluoride-rich phase to the first distillation column.

In another embodiment, the composition comprising HF and HFC-1234yf has a greater concentration of HF than the azeotrope composition for HF and HFC-1234yf. The excess HF may be removed from the bottom of the first distillation column and the azeotrope composition exits as the distillate. In another embodiment, the azeotrope composition comprising HF and HFC-1234yf may be condensed and cooled thereby forming two liquid phases, an HF-rich phase and an HFC-1234yf-rich phase. For this embodiment, the HF-rich phase is recycled back to the first distillation column and the HFC-1234yf-rich phase is fed to a second distillation column. As the HFC-1234yf-rich phase may have HFC-1234yf in excess of the azeotrope composition for HF/HFC-1234yf, the excess HFC-1234yf may be removed from the second distillation column bottom as HFC-1234yf essentially free of HF.

Referring again to FIG. 1, a composition comprising HF and HFC-1234yf is fed to a first column 110 via stream 100. This first column is operated under appropriate conditions to approach the low-boiling HF/HFC-1234yf azeotrope. Because HF is being fed to this first column in excess of that needed to form the azeotrope with the HFC-1234yf, HF is recovered as the bottoms of the column via stream 120, while a composition near to the HF/HFC-1234yf azeotrope is recovered as distillate via stream 130. Stream 130 is condensed in 140, mixed with a nearly azeotropic composition recycled from a second column via stream 250 and the combined stream is sub-cooled in cooler 160 and sent to decanter 180 where the combined stream 170 separates into a separate HF-rich stream 190 and an HFC-1234yf-rich stream 200. Stream 190 is recycled to the first column as reflux. Stream 200 is fed to the top stage of the second distillation column 210, operated under conditions to approach the HF/HFC-1234yf azeotrope. Because HFC-1234yf is being fed to this second column in excess of that needed to form the low-boiling HF/HFC-1234yf azeotrope, HFC-1234yf is recovered as the bottoms of the column via stream 220, while a composition close to the HF/HFC-1234yf azeotrope is recovered as distillate via stream 230. Stream 230 is condensed in 240, mixed with the nearly azeotropic composition from the first column via stream 150 and fed to cooler 160 and then decanter 180.

In one embodiment the operating conditions for the first and second distillation columns will depend upon the HFC- 1234yf being purified and the relative amounts of HF and HFC-1234yf in the composition to be separated.

In one embodiment, the first and second distillation column may operate at from about 14.7 psia (101 kPa) to about 300 psia (2068 kPa), with a top temperature of from about −50° C. to about 200° C. and a bottom temperature from about −30° C. to about 220° C. In another embodiment, the pressure will range from about 50 psia (345 kPa) to about 250 psia (1724 kPa), with a top temperature of from about −25° C. to about 100° C. and a bottom temperature from about 0° C. to about 150° C.

3. Separation Process—Azeotropic Distillation with an Entrainer

Azeotropic distillation for separating HFC-1234yf from mixtures of HF and HFC-1234yf may, in another embodiment, be carried out using an entrainer compound. For the process including an entrainer, the azeotrope composition need not phase separate upon condensing and cooling as described above.

In one embodiment, the entrainer serves to provide an improved liquid-liquid phase separation for a system wherein that separation would otherwise not be effective.

In one embodiment, the HFC-1234yf is present in the HF/HFC-1234yf mixture in a concentration greater than the azeotrope concentration for said HFC-1234yf and HF. Thus, in one embodiment is provided a process for the purification of HFC-1234yf from a mixture comprising HFC-1234yf and HF, wherein said HFC-1234yf is present in said mixture in a concentration greater than the azeotrope concentration for said HFC-1234yf and HF, said process comprising:

a. adding an entrainer to the mixture comprising HFC-1234yf and HF thus forming a second mixture;

b. distilling said second mixture in a first distillation step to form a first distillate composition comprising HF, HFC-1234yf, and entrainer, and a first bottoms composition comprising HFC-1234yf essentially free of HF and entrainer;

c. condensing said first distillate composition to form two liquid phases, being i) an HF-rich phase and ii) an entrainer-rich phase; and d. optionally recycling the entrainer-rich phase back to the first distillation step. In another embodiment, the process further comprises feeding the HF-rich phase to a second distillation step and forming a second distillate composition comprising entrainer, HFC-1234yf and HF and a bottoms composition comprising HF essentially free of HFC-1234yf and entrainer. In another embodiment, the process may further comprise recycling said second distillate composition back to the two liquid phases.

The process for separating HFC-1234yf from a first composition comprising HF and HFC-1234yf comprises contacting said first composition with an entrainer to form a second composition. The contacting may occur in a first distillation column, or the second composition may be formed by mixing the components prior to feeding to a distillation column in a pre-mixing step.

The weight ratio of the HF and HFC-1234yf in the first composition will depend upon the means of producing the composition. In one embodiment, the HF may be from about 3 weight percent to about 85 weight percent of the composition; the HFC-1234yf may be from about 97 weight percent to about 15 weight percent.

In another embodiment, the HF may be from about 5 weight percent to about 50 weight percent and the HFC-1234yf may be from about 95 weight percent to about 50 weight percent In yet another embodiment the composition comprising HF and HFC-1234yf may be produced in a dehydrofluorination reactor resulting in a 50/50 mole ratio of HF to the HFC-1234yf.

In one embodiment, the compositions comprising HF and HFC-1234yf may be prepared by any convenient method to combine the desired amounts of the individual components. A preferred method is to weigh the desired component amounts and thereafter combine the components in an appropriate vessel. Agitation may be used, if desired.

Alternatively, the compositions comprising HF and HFC-1234yf may be prepared by feeding the effluent from a reactor, including a dehydrofluorination reactor that contains HF and HFC-1234yf, to the first distillation column. The entrainer may be added at a separate feed point such that the second composition is formed directly in the distillation column. Alternatively, the entrainer may be mixed with the first composition comprising HF and HFC-1234yf thus forming the second composition prior to the distillation column in a pre-mixing step.

In one embodiment of the separation process, a composition comprising HFC-1234yf and HF is fed directly to a first distillation column. In another embodiment, the HFC-1234yf and HF may be pre-mixed with an entrainer prior to the distillation column. The pre-mixing step may occur in a cooler (160 in FIG. 2). Then the cooled mixture is fed to a decanter (180 in FIG. 2) prior to feeding to the distillation column.

In one embodiment, the first distillate composition comprises a low boiling azeotrope of HF and entrainer optionally containing minor amounts of HFC-1234yf. Further, in another embodiment, the HFC-1234yf essentially free of HF and optionally minor amounts of entrainer may be recovered from the bottom of the first distillation column.

The operating variables for the first distillation column will depend strongly on the entrainer being used in the separation process. In general the first distillation column may operate at pressures from about 14.7 psia (101 kPa) to about 500 psia (3448 kPa) with a top temperature of from about −50° C. to about 100° C. and a bottom temperature of from about −30° C. to about 200° C. In another embodiment, the first distillation column will operate at pressures from about 100 psia (690 kPa) to about 400 psia (2758 kPa) with a top temperature of from about −50° C. to about 50° C. and a bottom temperature from about 10° C. to about 150° C.

It was surprisingly calculated that in some few cases, azeotropes of HF and compounds used as entrainers will separate into HF-rich and entrainer-rich liquid fractions upon condensing and being cooled. In one embodiment, the first distillate composition may be fed to a liquid separation zone (e.g. decanter). The first distillate composition comprising an azeotrope of HF and entrainer may be phase separated forming two liquid phases, one being HF-rich and the other being entrainer-rich. The lower density phase may be recovered from the top of the liquid separation zone and the higher density phase may be recovered from the bottom of the liquid separation zone. The entrainer-rich phase (whether higher or lower density) may be fed back to the first distillation column. In one embodiment the HF-rich phase may be fed to a second distillation column or in another embodiment, the HF-rich phase may be split to send some portion back to the first distillation column (in order to provide more reflux and allow the first distillation column to operate properly) and the remainder may be fed to the second distillation column. The second distillation column allows recovery of HF essentially free of HFC-1234yf and entrainer as a bottoms composition. The top composition comprising HFC-1234yf, HF and entrainer may be recycled to the liquid separation zone, be utilized in some other manner, or disposed. The operating variables for the second distillation column will depend strongly on the entrainer being used in the separation process. In general the second distillation column may operate at pressures from about 14.7 psia (101 kPa) to about 500 psia (3448 kPa) with a top temperature of from about −50° C. to about 100° C. and a bottom temperature of from about −30° C. to about 200° C. In another embodiment, the first distillation column will operate at pressures from about 100 psia (690 kPa) to about 400 psia (2758 kPa) with a top temperature of from about −25° C. to about 50° C. and a bottom temperature from about zero ° C. to about 150° C.

Figure 2:
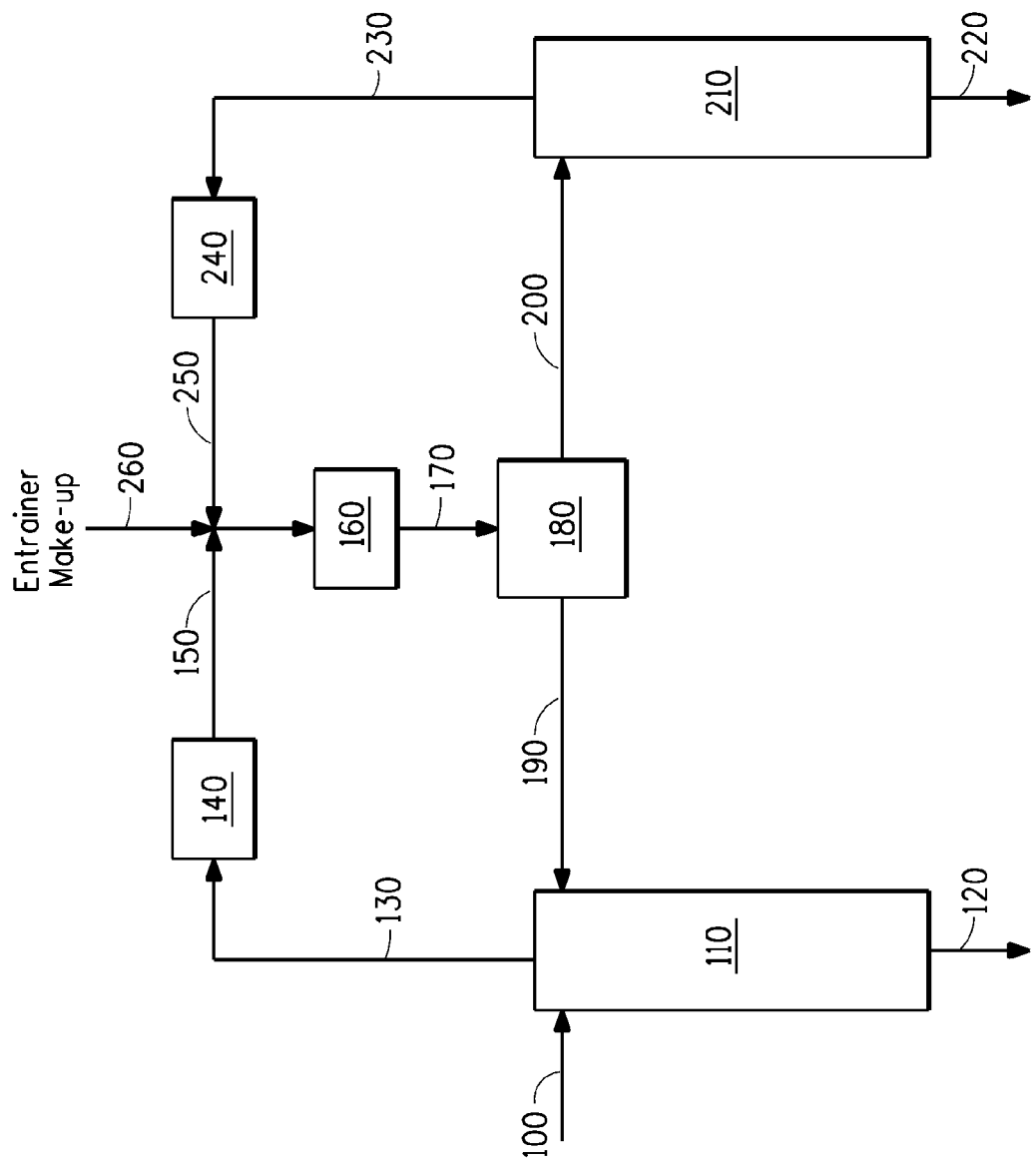
FIG. 2 is an illustration of one embodiment of an azeotropic distillation for the separation of HF and HFC-1234yf with an added entrainer.

Referring now to FIG. 2, a composition comprising HF and HFC-1234yf is fed to a first distillation column 110 via stream 100. An entrainer-rich composition is also fed to the top stage of column 110 via stream 190. If the combined amount of HFC-1234yf in streams 100 and 190 is in excess of that needed to form the low-boiling HF/HFC-1234yf azeotrope, HFC-1234yf is recovered essentially free of both HF and entrainer from the bottom of column 110 via stream 120. A ternary composition comprising HF, HFC-1234yf, and entrainer, but enriched in HFC-1234yf relative to stream 190, leaves the top of the first column as the first distillate stream 130. Stream 130 is condensed by condenser 140 forming stream 150 and mixed with a condensed second distillate stream 250 from a second distillation column. In one embodiment, additional entrainer may be added via stream 260, if needed. Combined streams 150, 250, and 260 are fed to cooler 160 and then to decanter 180 where the sub-cooled liquid stream 170 separates into entrainer-rich and HF-rich liquid phase compositions which leave the decanter via streams 190 and 200, respectively. The HFC-1234yf present distributes between the two liquid phases with the majority ending up in the entrainer-rich phase. The HF-rich composition stream 200 is fed to the top stage of the second distillation column 210. Because the amount of HF in stream 200 is in excess of that needed to form a low-boiling HF/HFC-1234yf azeotrope, HF is recovered as a product stream essentially free of both HFC-1234yf and entrainer from the bottom of column 210 via stream 220. A ternary composition comprising HF, HFC-1234yf and entrainer, but enriched in entrainer relative to stream 200, leaves the top of the second column as the second distillate stream 230. Stream 230 is condensed in condenser 240, forming stream 250, and combined with streams 150 and 260 previously described.

Alternatively, in another embodiment, rather than feed the HF/HFC-1234yf mixture directly to the distillation column 110, the mixture may be fed to cooler 160 and then to decanter 180 where the mixture phase separates. Then stream 190 carries the mixture of HF, HFC-1234yf and entrainer to the first distillation column 110.

In another embodiment, the concentration of HF in the HF/HFC-1234yf mixture is greater than the concentration in the azeotrope of HFC-1234yf and HF. Thus, in another embodiment is provided a process for the purification of HF from a mixture comprising HFC-1234yf and HF, wherein HF is present in a concentration greater than the azeotrope concentration for HF and said HFC-1234yf, said process comprising:

a. adding an entrainer to the mixture comprising HFC-1234yf and HF thus forming a second mixture;

b. distilling said second mixture in a first distillation step to form a first distillate composition comprising HF, entrainer, and an HFC-1234yf, and a first bottoms composition comprising HF essentially free of HFC-1234yf and entrainer;

c. condensing said first distillate composition to form two liquid phases, being i) an entrainer-rich phase and ii) an HF-rich phase; and d. optionally recycling the HF-rich phase back to the first distillation step. In another embodiment, the process may further comprising feeding the HF-rich phase to a second distillation step and forming a second distillate composition comprising entrainer, HF, and HFC-1234yf, and a bottoms composition comprising HFC-1234yf essentially free of entrainer. In another embodiment, the process may further comprise recycling said second distillate composition back to the two liquid phases.

Referring again to FIG. 2, a composition comprising HF and HFC-1234yf is fed to a first distillation column 110 via stream 100. An HF-rich composition is also fed to the top stage of column 110 via stream 190. If the combined amount of HF in streams 100 and 190 is in excess of that needed to form the low-boiling HF/HFC-1234yf azeotrope, HF is recovered essentially free of both HFC-1234yf and entrainer from the bottom of column 110 via stream 120. A composition near the HF/HFC-1234yf azeotrope with a minor amount of entrainer is recovered as the first distillate via stream 130. Stream 130 is condensed by condenser 140 forming stream 150 and mixed with a condensed second distillate stream 250 from a second distillation column. In one embodiment, additional entrainer may be added via stream 260, if needed. Combined streams 150, 250, and 260 are fed to cooler 160 and then to decanter 180 where the sub-cooled liquid stream 170 separates into HF-rich and entrainer-rich liquid phase compositions which leave the decanter via streams 190 and 200, respectively. The HFC-1234yf present distributes between the two liquid phases with the majority ending up in the entrainer-rich phase. The entrainer-rich composition stream 200 is fed to the top stage of the second distillation column 210. Because the amount of HFC-1234yf in stream 200 is in excess of that needed to form a low-boiling entrainer/HFC-1234yf azeotrope, HFC-1234yf is recovered as a product stream essentially free of both HF and entrainer from the bottom of column 210 via stream 220. A ternary composition comprising entrainer, HFC-1234yf, and HF, but enriched in entrainer relative to stream 200 leaves the top of the second column as the second distillate stream 230. Stream 230 is condensed in condenser 240, forming stream 250, and combined with streams 150 and 260 previously described.

Alternatively, in another embodiment, rather than feed the HF/HFC-1234yf mixture directly to the distillation column 110, the mixture may be fed to cooler 160 and then to decanter 180 where the mixture phase separates. Then stream 190 carries the mixture of HF, HFC-1234yf and entrainer as the HF-rich phase to the first distillation column 110.

4. Separation of HFC-245 from HFC-1234yf and HF

HFC-1234yf is a valuable fluorocarbon useful as a refrigerant, blowing agent, aerosol propellant, and sterilant among other uses.

HFC-1234yf may be produced by dehydrofluorination of certain HFC-245 (pentafluoropropane) isomers. By HFC-245 is meant any isomer of pentafluoropropane and any combinations of any isomers of pentafluoropropane that can yield HFC-1234yf upon dehydrofluorination. Isomers of pentafluoropropane include HFC-245eb (1,1,1,2,3-pentafluoropropane) and HFC-245cb (1,1,1,2,2-pentafluoropropane).

HFC-1234yf may be prepared by the vapor phase dehydrofluorination of HFC-245eb or HFC-245cb by processes such as those described in U.S. Pat. Nos. 2,931,840, 2,996, 555, or 7,189,884. For example, HFC-1234yf can be prepared by passing HFC-245eb, HFC-245cb or mixtures of HFC-245eb and HFC-245cb over a chrome oxide catalyst at elevated temperatures, for example, at above 300° C. The product stream from this reaction contains HFC-1234yf, HF and any unreacted HFC-245eb and/or HFC-245cb.

In one embodiment, a process is provided for the separation of HFC-1234yf from a mixture of HFC-1234yf, HF, and at least one of HFC-245eb or HFC-245cb, said process comprising:

a) subjecting said mixture to a first distillation step, wherein additional HFC-1234yf is fed from a second distillation step, to form a first distillate comprising an azeotrope of HFC-1234yf and HF and a first bottoms composition comprising at least one of HFC-245eb or HFC-245cb;

b) feeding said first distillate to a second distillation step to form a second distillate comprising an azeotrope of HFC-1234yf and HF and a second bottoms composition comprising HFC-1234yf essentially free of HF;

c) condensing said second distillate to form two liquid phases, being i) an HF-rich phase and ii) an HFC-1234yf-rich phase; and d) recycling the HFC-1234yf-rich phase from (c) back to the second distillation step. In another embodiment, the process may further comprise feeding the HF-rich phase to a third distillation step to form a third distillate comprising an azeotrope of HFC-1234yf and HF and a third bottoms composition comprising HF essentially free of HFC-1234yf.

In this embodiment the azeotropic distillation involves providing an excess of HFC-1234yf to the distillation column in addition to that produced from the dehydrofluorination reaction of HFC-245eb and/or HFC-245cb. In this embodiment, HFC-1234yf serves as an entrainer in the distillation process. If the proper total amount of HFC-1234yf is fed to the column, then all the HF may be taken overhead as an azeotrope composition containing HFC-1234yf and HF. Enough HFC-1234yf can be provided, for example, by feeding supplemental HFC-1234yf to the distillation column over that exiting in the dehydrofluorination reaction product stream. Thus, the HFC-245eb and/or HFC-245cb removed from the column bottoms may be essentially free of HF.

For example, a reactor product mixture comprising HF, HFC-1234yf and HFC-245eb may be fed to a first distillation column operated under conditions to form the HF/HFC-1234yf azeotrope with the HF/HFC-1234yf azeotrope being removed from the distillation column as the overhead distillate. The HF in this distillate may then be separated and removed from the HFC-1234yf by other means, e.g. by using pressure swing distillation or the methods as disclosed herein. Some portion of the HFC-1234yf so obtained can be recycled back to the first distillation column in quantities sufficient so that all the HF fed to the first distillation column is removed from that column as the HF/HFC-1234yf azeotrope, thus producing a HFC-245eb bottoms stream essentially free of HF.

Where the composition to be separated is formed by dehydrohalogenation of either of HFC-245eb or HFC-245cb, it is desirable to recycle any unreacted HFC-245eb or HFC-245cb back to the reactor so that they may be converted to HFC-1234yf. However, it is necessary that HF and HFC-1234yf be removed from said unreacted HFC-245eb or HFC-245cb prior to being recycled so as not to inhibit the equilibrium reaction. It is also necessary that the HF be removed from the HFC-1234yf to allow its use as a refrigerant or in other applications.

Figure 3:
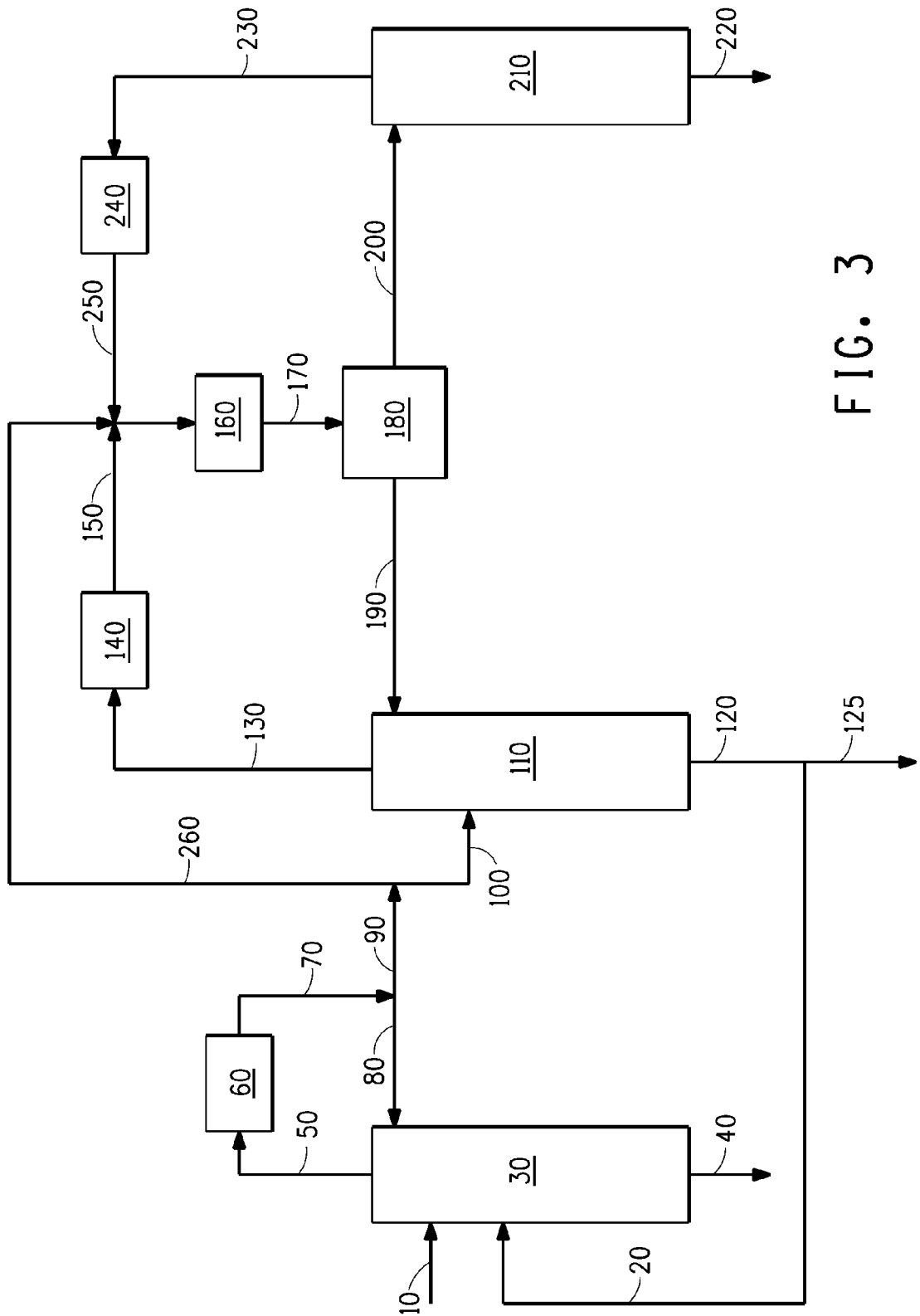
FIG. 3 is an illustration of one embodiment of a process to separate at least one of HFC-245eb or HFC-245cb from a mixture comprising HFC-1234yf, HF and said at least one of HFC-245eb or HFC-245cb via azeotropic distillation wherein HFC-1234yf acts as an entrainer followed by a process in which HFC-1234yf and HF are separated from a mixture comprising HFC-1234yf and HF, but now substantially free of HFC-245eb and/or HFC-245cb, by azeotropic distillation without the addition of another chemical compound to function as an entrainer.

Referring now to FIG. 3, a stream comprising HF, HFC-1234yf, and at least one of HFC-245eb or HFC-245cb is fed to a first distillation column via stream 10, with the column operated under conditions to approach the low-boiling HF/HFC-1234yf azeotrope, which is removed as distillate via streams 50, 70, and 90. Enough supplemental HFC-1234yf is recycled from the second column bottoms to this first column via stream 20 to enable all of the HF to be removed from the HFC-245cb and/or HFC-245eb. The HFC-245cb and/or HFC-245eb are obtained essentially free of HFC-1234yf and HF as the bottoms product from this column via stream 40.

The near HF/HFC-1234yf azeotropic composition in stream 50 is condensed and divided into reflux 80 and distillate 90 streams. Distillate stream 90 may be fed to a second distillation column 110 via stream 100 as shown and indicated, mixed with distillate streams 150 and 250 from the second and third columns, respectively, and sent to cooler 160 and decanter 180, or be divided between these two destinations. Because of the desire to remove all of the HF overhead in column 30, excess HFC-1234yf would be recycled to column 30, making the composition of streams 50, 70, 80, 90, and 100 lie on the HFC-1234yf-rich side of the azeotrope. Therefore, if distillate stream 90 is sent via stream 100 to a second distillation column, it should be sent to the column which produces purified HFC-1234yf as the bottoms product.

In one embodiment, distillate stream 90 via stream 260 is mixed with distillate streams 150 and 250 from the second and third columns, respectively, and sent to cooler 160, forming sub-cooled stream 170, which is fed to decanter 180. In the decanter, stream 170 separates into HFC-1234yf-rich and HF-rich liquid fractions, which are removed as streams 190 and 200. The HFC-1234yf-rich stream from the decanter is fed via stream 190 to a second distillation column 110 containing 19 theoretical stages and operated under conditions to approach the HFC-1234yf/HF azeotrope, which is distilled overhead as distillate stream 130, condensed in condenser 140, and mixed with the distillates from the first and third columns via stream 150. Column 110 produces a bottoms stream of HFC-1234yf essentially free of HF via stream 120. Part of the HFC-1234yf bottoms stream 120 is recycled to the first column via stream 20, as previously described, and the rest becomes the purified HFC-1234yf product removed via stream 125. The HF-rich stream from the decanter is fed via stream 200 to a third distillation column 210 operated under conditions to approach the HFC-1234yf/HF azeotrope, which is distilled overhead as distillate as stream 230 which is condensed in condenser 250 and mixed with the distillates from the first and second columns via stream 250. Column 210 produces a bottoms stream of HF essentially free of HFC-1234yf via stream 220.

In another aspect of this invention, an entrainer may be added to enable separation of the HF from the HFC-1234yf, or separation of the HF from the HFC-1234yf and HFC-245eb and/or HFC-245cb.

For example, the mixture of HF, HFC-1234yf, HFC-245eb and/or HFC-245cb may be formed by any practical means, such as by feeding at least one of HFC-245cb or HFC-245eb over a chrome oxide catalyst at elevated temperature. The mixture of HF, HFC-1234yf, HFC-245eb and/or HFC-245cb may be fed to a distillation column. A suitable entrainer is then also fed to the distillation column, either as a separate stream or by being mixed in with the HF/HFC-1234yf/HFC-245cb and/or HFC-245eb mixture prior to feeding it to the distillation column. The distillation column is then operated under conditions sufficient to form a low-boiling azeotrope composition between the entrainer and HF, with the HF and entrainer removed as the column distillate, and the HFC-1234yf, HFC-245eb and/or HFC-245cb recovered from the column bottoms essentially free of HF. The HFC-1234yf may then be separated from the HFC-245eb and/or HFC-245cb by any usual means including conventional distillation, with the HFC-1234yf being recovered as product and with the HFC-245eb and/or HFC-245cb optionally being recycled back to the reaction step to produce HFC-1234yf.

Thus in another embodiment is provided a process for separating HF from a mixture comprising HFC-1234yf, HF, and at least one of HFC-245eb or HFC-245cb. The process comprises:

a. adding an entrainer to the mixture comprising HFC-1234yf, HF, and at least one of HFC-245eb or HFC-245cb thus forming a second mixture;

b. distilling said second mixture in a first distillation step to form a first distillate composition comprising HF and entrainer and a first bottoms composition comprising HFC-1234yf and at least one of HFC-245eb or HFC-245cb;

c. condensing said first distillate composition to form two liquid phases, being (i) an entrainer-rich phase and (ii) an HF-rich phase; and d. recycling the entrainer-rich phase back to the first distillation step.

In another embodiment, the process may further comprise feeding the HF-rich phase to a second distillation step and forming a second distillate composition comprising an azeotrope of entrainer and HF and a second bottoms composition comprising HF essentially free of entrainer. In another embodiment, the process may further comprise recycling said second distillate composition back to the two liquid phases.

Figure 4:
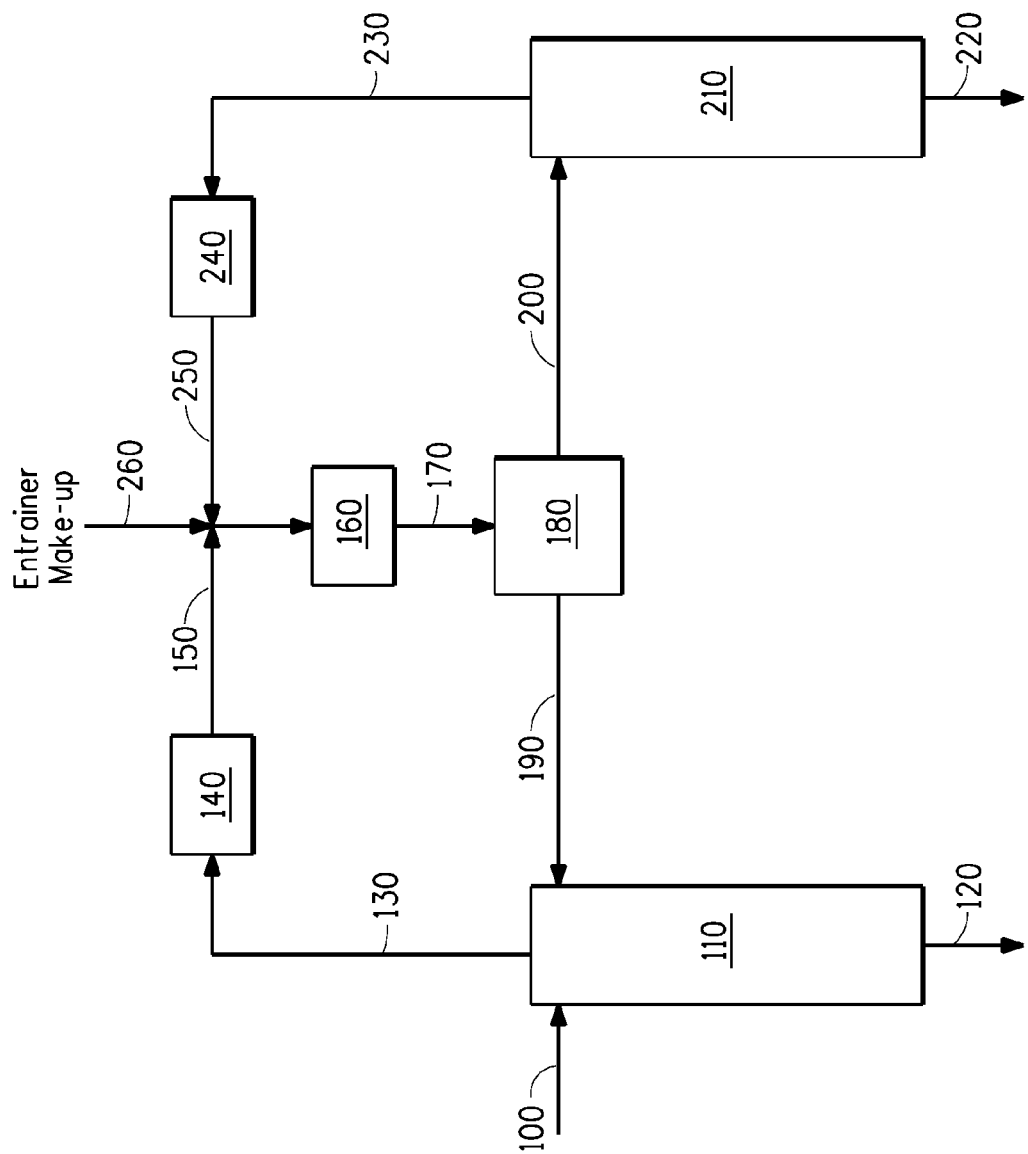
FIG. 4 is an illustration of one embodiment of a process to separate HFC-1234yf and at least one of HFC-245eb or HFC-245cb from a mixture comprising HFC-1234yf, HF and said at least one of HFC-245eb or HFC-245cb via azeotropic distillation wherein a supplemental entrainer is fed to the distillation.

Referring now to FIG. 4, a stream comprising HF, HFC-1234yf, and at least one of HFC-245eb or HFC-245cb is fed to a first distillation column 110 via stream 100. An entrainer-rich stream is also fed to this column via stream 190. Column 110 is operated under conditions to cause HF to distill overhead with the entrainer due to the influence of the low-boiling HF/entrainer azeotrope. Sufficient entrainer is fed to this first column via stream 190 such that HFC-1234yf and HFC-245eb or HFC-245cb may be obtained essentially free of entrainer and HF as the bottoms from column 110 via stream 120. The HFC-1234yf and HFC-245eb or HFC-245cb in stream 120 may then optionally be separated from each other by conventional distillation and the HFC-245eb or HFC-245cb optionally recycled back to a dehydrofluorination reactor to form HFC-1234yf. The distillate from column 110, removed via stream 130, contains essentially all of the entrainer and HF in column feeds 100 and 190 and, optionally, some HFC-245eb or HFC-245cb and/or HFC-1234yf. This first distillate stream 130 is condensed by condenser 140 to form stream 150, which is then mixed with condensed distillate stream 250 from the second distillation column and, as needed, additional fresh entrainer added via stream 260. This combined stream is sub-cooled by cooler 160 and sent via stream 170 to decanter 180 where it separates into separate entrainer-rich and HF-rich liquid fractions which are removed via streams 190 and 200, respectively. The majority of the HFC-245eb or HFC-245cb and HFC-1234yf present in the decanter partition into the entrainer-rich phase fraction. The entrainer-rich fraction is fed to the first distillation column 110 via stream 190. The HF-rich fraction from the decanter is fed via stream 200 to a second distillation column 210 containing 8 theoretical stages and operated under conditions such that a bottoms stream of HF essentially free of HFC-245eb or HFC-245cb, HFC-1234yf, and entrainer is produced and removed via stream 220. The distillate from column 210, removed via stream 230 and containing essentially all of the HFC-245eb or HFC-245cb, HFC-1234yf, and entrainer present in the column feed (stream 200) plus the HF not recovered in product stream 220, is condensed by condenser 240 and removed via stream 250. Condensed distillate stream 250 is combined with both the condensed distillate stream 150 from the first column and, as needed, fresh entrainer, added via stream 260, then cooled and fed to the decanter for further separation.

In another embodiment, HFC-245eb and/or HFC-245cb, which form homogeneous azeotropes with HF, can be separated from a mixture comprising HF, HFC-245eb and/or HFC-245cb, and HFC-1234yf by azeotropic distillation using the HFC-1234yf as an entrainer, followed by separation of the HFC-1234yf and HF by azeotropic distillation using an added compound as the entrainer. HF and the HFC-1234yf are not required to be partially miscible at reduced temperatures for such a separation process to work as long as the HF-HFC-1234yf azeotrope has a lower boiling point than the HF-HFC-245eb azeotrope and/or HF-HFC-245cb azeotrope.

Figure 5:
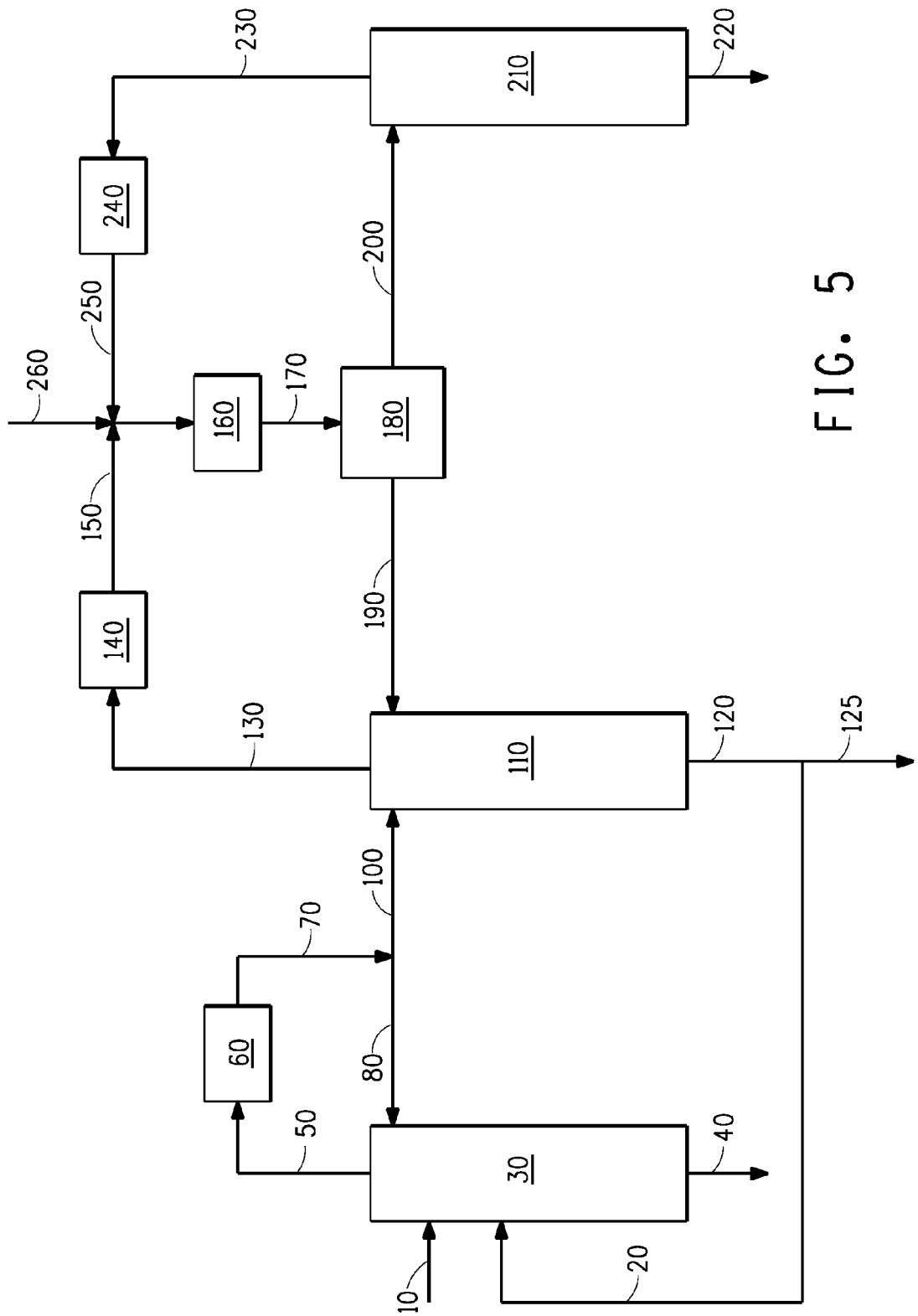
FIG. 5 is an illustration of one embodiment of a process to separate at least one of HFC-245eb or HFC-245cb from a mixture comprising HFC-1234yf, HF and said at least one of HFC-245eb or HFC-245cb via azeotropic distillation wherein HFC-1234yf acts as an entrainer followed by a process in which HFC-1234yf and HF are separated from a mixture comprising HFC-1234yf and HF, but now substantially free of HFC-245eb and/or HFC-245cb, by azeotropic distillation with an added entrainer.

Referring now to FIG. 5, a stream comprising HF, HFC-1234yf, and at least one of HFC-245eb or HFC-245cb is fed to a first distillation column 30 via stream 10, with the column operated under conditions to approach the low-boiling HF/HFC-1234yf azeotrope, which is removed as distillate via streams 50, 70, and 100. This first column can be designed and operated in such a way that the near azeotropic distillate is essentially free of HFC-245eb and/or HFC-245cb. By recycling enough supplemental HFC-1234yf from the second column bottoms to the first column via stream 20, essentially all of the HF can be distilled overhead as the HF/HFC-1234yf azeotrope such that HFC-245cb and/or HFC-245eb are obtained essentially free of HFC-1234yf and HF as the bottoms product from column 30 via stream 40. The HFC-245eb and/or HFC-245cb may then optionally be recycled back to a reactor for production of HFC-1234yf, or may be further purified and then recycled. This demonstrates the use of HFC-1234yf as an entrainer to remove HF from HFC-245cb and/or HFC-245eb.

As described for FIG. 3, the distillate from the first column may be fed to a second distillation column, mixed with the distillate streams from a second and third column, cooled, and then sent to a decanter, or split between these two destinations. In this embodiment (FIG. 5), the distillate from the first column 30 is fed via stream 100 to a second column 110. An entrainer-rich stream is also fed to this second column via stream 190. Distillation column 110 is operated under conditions such that the distillate, removed via stream 130, contains essentially all of the entrainer and HF in the column feeds 100 and 190 and produces an HFC-1234yf bottoms product essentially free of HF and entrainer which is removed via stream 120. Part of the HFC-1234yf bottoms stream 120 is recycled to the first column via stream 20, as previously described, and the rest becomes the purified HFC-1234yf product removed via stream 125. Distillate stream 130 is condensed by condenser 140 to form stream 150, which is then mixed with the condensed distillate stream 250 from the second distillation column and, as needed, fresh entrainer added via stream 260. This combined stream is cooled by cooler 160 and sent via stream 170 to decanter 180 where it separates into separate entrainer-rich and HF-rich liquid fractions, which are removed via streams 190 and 200, respectively. The majority of the HFC-1234yf present in the decanter partitions into the entrainer-rich phase fraction. The decanter entrainer-rich fraction is fed to column 110 via stream 190. The decanter HF-rich fraction is fed, via stream 200, to a third distillation column 210 operated under conditions which produce a bottoms product consisting of HF essentially free of HFC-1234yf and the entrainer, which is removed via stream 220. The distillate from column 210, which is removed via stream 230 and contains essentially all of the HFC-1234yf and entrainer present in the column feed (stream 200) and any HF not recovered in product stream 220, is condensed by condenser 240, forming stream 250. Condensed distillate stream 250 is combined with both the condensed distillate stream 150 from the second column and, as needed, fresh entrainer, added via stream 260, then cooled and fed to the decanter via stream 170 for further separation.

In one embodiment, entrainers for HF separation from HFC-1234yf and optionally HFC-245eb and/or HFC-245cb include: methane, ethane, ethylene, acetylene, vinylacetylene, n-propane, propylene, propyne, cyclopropane, cyclopropene, propadiene, methyl chloride ($CH_3Cl$), dichlorodifluoromethane (CFC-12), 2-chloro-1,1,2-trifluoroethylene, chloropentafluoroethane (CFC-115), 2-chloro-1,1,3,3,3-pentafluoropropene (CFC-1215xc), 2-chloro-1,1-difluoroethylene (HCFC-1122), 1,1,2-trifluoroethylene (HFC-1123), 1,1-difluoroethylene (HFC-1132a), 2,3,3,3-tetrafluoropropene (HFC-1234yf), hexafluoroethane (PFC-116), octafluoropropane (PFC-218), 1,1,1,4,4,4-hexafluoro-2-butyne (PFBY-2), hexafluoropropylene (HFP, PFC-1216), hexafluorocyclopropane (PFC-C216), trifluoromethyl-difluoromethyl ether ($CF_3OCHF_2$, HFOC-125E), 1,1-difluorodimethyl ether, tetrafluorodimethylether (HFOC-134E), difluoromethyl methyl ether ($CHF_2OCH_3$, HFOC-152aE), pentafluoroethyl methyl ether, HFPO, chlorine ($Cl_2$), hexafluoroacetone, PMVE (perfluoromethylvinylether), PEVE (perfluoroethylvinylether), and mixtures thereof.

In another embodiment, the entrainers that are effective for separation of HF from HFC-1234yf and optionally HFC-245eb and/or HFC-245cb include n-propane and CFC-115.

Figure 6:
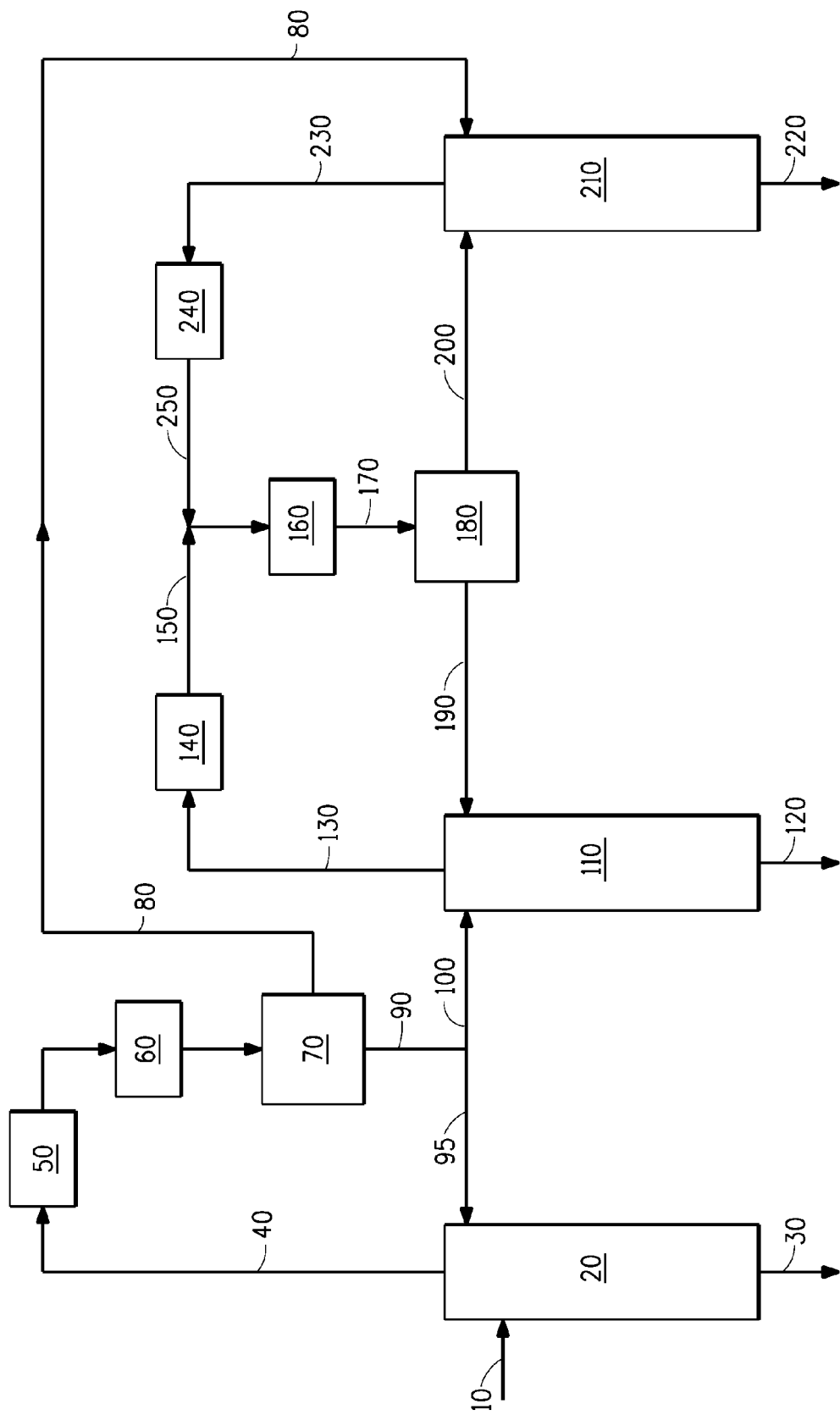
FIG. 6 illustrates another embodiment of the process shown in FIG. 3 wherein the two-phase mixture leaving the condenser of the first column is decanted and separated into HFC-1234yf-rich and HF-rich streams which are fed to the HFC-1234yf and HF columns, respectively.

In another embodiment, a condenser 50, cooler 60, and decanter 70 can be added to the distillate stream coming from the first distillation column. This embodiment is illustrated in FIG. 6. Referring now to FIG. 6, a first cooler 60 and a first decanter 70 are added after the first distillation column's condenser 50 such that the distillate separates into HF-rich and HFC-1234yf-rich liquid phase fractions in the decanter, which are removed via streams 80 and 90, respectively. Part of the HFC-1234yf-rich stream 90 is returned to the first column as reflux via stream 95 and the remaining portion is fed to a second distillation column 110 via stream 100 where it is separated into an HFC-1234yf bottoms product, removed via stream 120, that is essentially free of HF and a distillate composition near to the HF/HFC-1234yf azeotrope, removed via stream 130. Because the reflux stream 95 is enriched in HFC-1234yf relative to the HFC-1234yf/HF azeotropic composition, the reflux stream 95 supplies the additional HFC-1234yf needed to make the HFC-245eb and/or HFC-245cb bottoms product from the first column, removed via stream 30, essentially free of HF, thereby reducing the amount of purified HFC-1234yf that must be recycled from the second column to the first column. As shown in FIG. 6, for this embodiment, at sufficiently high reflux flows, the need for recycling any of the purified HFC-1234yf from the bottom of the second column to the first column can be completely eliminated. The first decanter's HF-rich phase fraction is fed to a third distillation column 210 via stream 80. Both feeds (streams 80 and 200) to the third column have compositions containing excess HF relative to the HF/HFC-1234yf azeotrope so that an HF bottoms product essentially free of HFC-1234yf may be obtained in column 210 and removed via stream 220. The distillate from the third column has a composition near to the HF/HFC-1234yf azeotrope and is removed via stream 230. The distillates (streams 130 and 230) from columns 110 and 210 are condensed in condensers 140 and 240, forming streams 150 and 250, respectively, mixed together, and sent first to a second cooler 160 and then to a second decanter 180 where separate HFC-1234yf-rich and HF-rich liquid phase fractions are formed. The HFC-1234yf-rich fraction is removed from decanter 180 via stream 190 and fed to the second column 110 for further separation. The HF-rich fraction is removed from decanter 180 via stream 200 and fed to the third column 210 for further separation. This demonstrates how the HFC-1234yf can allow the separations without the need for an added entrainer.

In another embodiment, if the HFC-1234yf/HF azeotrope has a lower boiling point than the HFC-245/HF azeotrope (meaning either or both of the HFC-245eb/HF and HFC-245cb/HF azeotropes), then HFC-1234yf can be used as the entrainer to remove the HFC-245 from the mixture. The HFC-1234yf and HF can be separated either by using the fluoroolefin as the entrainer, as shown and described for FIG. 6 or by using an added compound as the entrainer. The case where an added entrainer is used is shown in FIG. 7.

Figure 7:
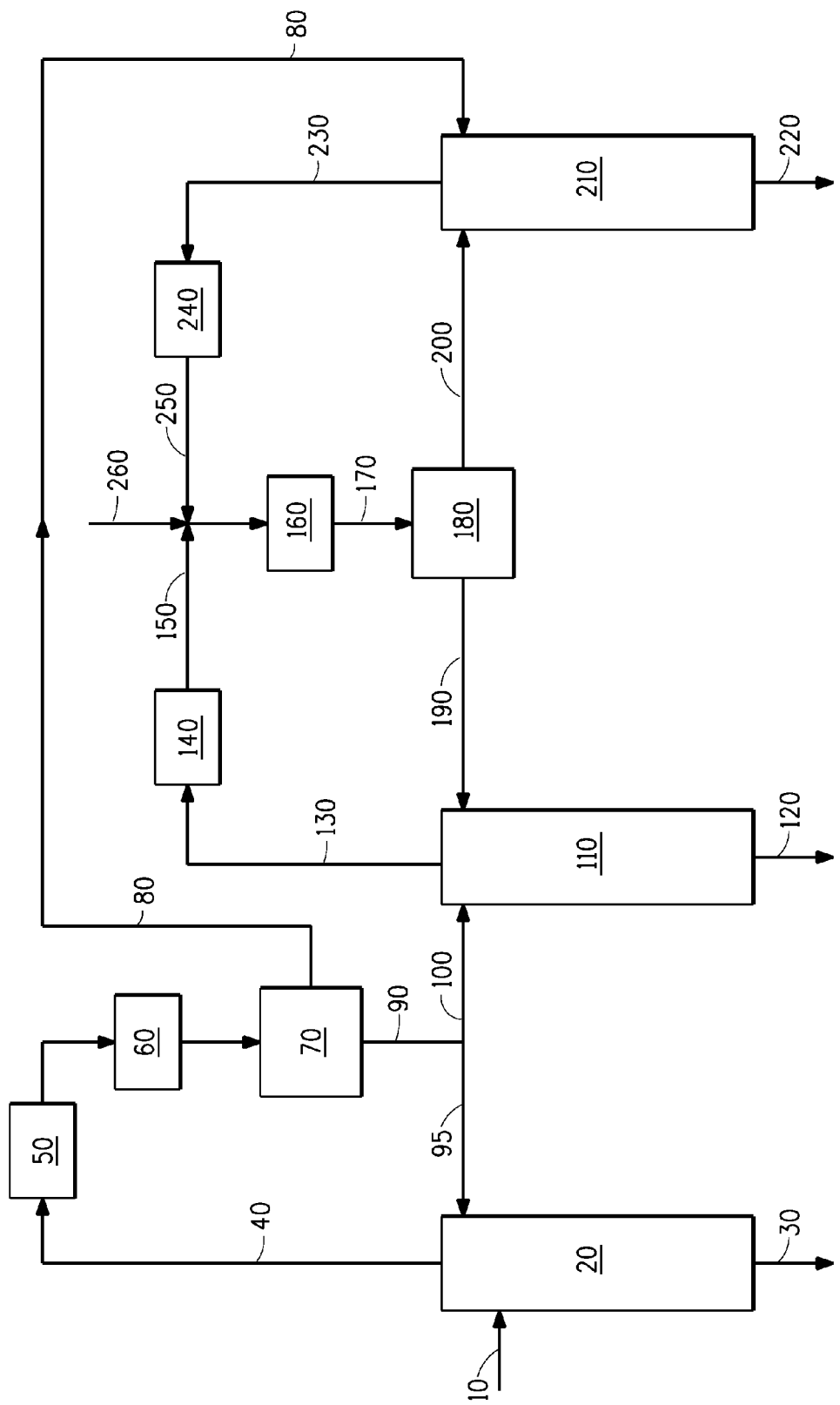
FIG. 7 illustrates another embodiment of the process shown in FIG. 5 wherein the two-phase mixture leaving the condenser of the first column is decanted and separated into HFC-1234yf-rich and HF-rich streams which are fed to the HFC-1234yf and HF columns, respectively.

Referring now to FIG. 7, the first distillation column 20, condenser 50, cooler 60, and decanter 70 in this embodiment operates identically to the similarly numbered equipment in FIG. 6 as just described. The HF-rich and HFC-1234yf-rich liquid distillate fractions from the first column's decanter 70 are fed via streams 80 and 100 to distillation columns 210 and 110 which recover purified HF and HFC-1234yf, respectively. The remaining portion of the process shown in FIG. 7, i.e., distillation columns 110 and 210, condensers 140 and 240, cooler 160, decanter 180, and all of their associated streams, have the same function and operate similarly to the same numbered equipment shown and described for FIG. 5.

In other embodiments of the invention, certain pieces of equipment can serve multiple distillation columns. For instance, in one embodiment, condensers 140 and 240 may be combined into a single unit, thus streams 130 and 230 of FIG. 7 would both feed into the single condenser. In another embodiment, coolers 60 and 160 of FIG. 7 can be combined into a single unit, shown as cooler 160 in FIG. 8. In another embodiment, decanters 70 and 180 of FIG. 7 can be combined into a single unit, as shown by decanter 180 in FIG. 8. In yet another embodiment, the three condensers 50, 140 and 240 of FIG. 7 can be combined into a single unit, thus streams 40, 130 and 230 of FIG. 7 would all feed into the one condenser.

5. Separation of Products from the Co-production of HFC-1234yf and HFC-1225ye

It has been found that the HFC-1234yf/HF azeotrope may also be used to benefit in the co-production of HFC-1225ye and HFC-1234yf. HFC-1225ye may be produced from the dehydrofluorination of HFC-236ea ($CF_3CHFCHF_2$, 1,1,1,2,3,3-hexafluoropropane) and/or HFC-236cb ($CF_3CF_2CH_2F$, 1,1,1,2,2,3-hexafluoropropane). If HFC-236ea and/or HFC-236cb and HFC-245cb and/or HFC-245eb are co-fed to a reactor containing a suitable dehydrofluorination catalyst and operating at a suitable temperature, a mixture comprising HFC-1225ye, HFC-1234yf, HF, unreacted HFC-236ea and/or HFC-236cb, and unreacted HFC-245cb and/or HFC-245eb, would be produced. The separation of HFC-1234yf from HFC-1225ye will be difficult by conventional distillation processes.

Each of HFC-1234yf, HFC-1225ye, HFC-245eb, HFC-245cb, HFC-236ea, and HFC-236cb form an azeotrope composition with HF. The HFC-1234yf/HF azeotrope has the lowest normal boiling point of all these azeotropes, followed by the HFC-1225ye/HF azeotrope, and the HFC-245cb/HF azeotrope.

In one embodiment, a process is provided for separating HFC-1225ye from HFC-1234yf, said process comprising a) feeding a mixture of HFC-236ea and/or HFC-236cb, HFC- 245eb and/or HFC-245cb, HFC-1234yf, HFC-1225ye, and HF to a first distillation column; b) removing an azeotrope composition comprising HFC-1234yf and HF as a first distillate composition; and c) removing a composition comprising HFC-236ea and/or HFC-236cb, HFC-245eb and/or HFC-245cb, and HFC-1225ye as a first bottoms composition.

In another embodiment, the first bottoms composition may comprise HFC-236ea and/or HFC-236cb, HFC-245eb and/or HFC-245cb, and HFC-1225ye essentially free of HF. For this embodiment, there must be enough HFC-1234yf present to azeotrope all of the HF in the mixture. In one embodiment, purified HFC-1234yf may be fed to the distillation column along with the mixture. In another embodiment, the first distillate composition may be condensed to form two liquid phases and fed to a decanter as described previously herein. Then the HFC-1234yf-rich phase from the decanter may be fed back to the first distillation column.

In another embodiment, the first bottoms composition comprising HFC-236ea and/or HFC-236cb, HFC-245eb and/or HFC-245cb, and HFC-1225ye may be separated by any known means such as for instance conventional fractional distillation.

In one embodiment, the first distillate composition may be treated to separate the HFC-1234yf and HF by processes such as those described herein, and thus produce HFC-1234yf essentially free of HF.

In another embodiment, wherein there is no HFC-245cb present in the mixture, both the HFC-1234yf and HFC-1225ye azeotropes can be used to produce an essentially HF-free mixture containing HFC-236ea and/or HFC-236cb and HFC-245eb. In this embodiment, the process comprises a) feeding a first mixture comprising HFC-236ea and/or HFC-236cb, HFC-245eb, HFC-1234yf, HFC-1225ye, and HF to a first distillation column; b) removing a second mixture comprising azeotrope compositions of HFC-1234yf and HF and HFC-1225ye and HF as a first distillation composition; and c) removing a third mixture comprising HFC-236ea and/or HFC-236cb and HFC-245eb essentially free of HF. In another embodiment, the HF-free mixture of HFC-236ea and/or HFC-236cb and HFC-245eb can be recycled to the dehydrofluorination reactor for further reaction to HFC-1225ye and/or HFC-1234yf.

The distillate from this first column would consist of all the HF and HFC-1225ye and HFC-1234yf product formed in the reactor. The HF could be separated from the fluoroolefins by azeotropic distillation with or without an added entrainer as described previously herein, leaving HFC-1225ye and HFC-1234yf essentially free of HF, which can subsequently be separated by ordinary fractional distillation.

In any of the embodiments as described and illustrated for FIGS. 3, 5, 6, and 7, an entrainer may be added to the first distillation step to assist in removing the hydrogen fluoride from the at least one of HFC-245eb or HFC-245cb. This variation is intended to fall within the scope of the claims.

EXAMPLES

The concepts described herein will be further described in the following examples, which do not limit the scope of the invention described in the claims.

Example 1

Synthesis of HFC-1234yf by Dehydrofluorination with Fluorided Alumina Catalyst

A Hastelloy® tube reactor (1.0" OD×0.854" ID×9.5" L) was filled with 25 cc of gamma-alumina ground to 12-20 mesh. The packed portion of the reactor was heated by a 5"×1" ceramic band heater clamped to the outside of the reactor. A thermocouple, positioned between the reactor wall and the heater measured the reactor temperature. The catalyst was dried by heating at 200° C. for 15 minutes under a nitrogen purge and then reacted with a HF/$N_2$ mixture heated up to 425° C. to yield 16.7 gm of activated fluorided alumina.

At a temperature of 350° C., 10 sccm of nitrogen ($1.7 \times 10^{-7}$ $m^3/s$) and 15 sccm ($2.5 \times 10^{-7}$ $m^3/s$) of HFC-245cb ($CF_3CF_2CH_3$) were mixed and flowed through the reactor. The temperature was then raised to 400° C., the flow rates held constant. The effluent for both temperatures was sampled and analyzed by $^{19}F$ NMR. Additionally, the effluent was analyzed by GC/FID to determine concentrations as listed in Table 1.

TABLE 1

| Temp., | $N_2$ flow | HFC-245cb | Concentrations, (GC/FID area %) | | |
|---|---|---|---|---|---|
| ° C. | (sccm) | flow (sccm) | HFC-1234yf | HFC-245cb | Unknowns |
| 350 | 10 | 15 | 84.2 | 12.8 | 3.0 |
| 400 | 10 | 15 | 91.3 | 1.9 | 6.8 |

Example 2

Synthesis of HFC-1234yf with Carbon Catalyst

To a Hastelloy® nickel alloy reactor (1.0" OD×0.854" ID×9.5" L) was charged 14.5 g (25 mL) of spherical (8 mesh) three dimensional matrix porous carbonaceous material prepared substantially as described in U.S. Pat. No. 4,978,649, incorporated herein by reference. The packed portion of the reactor was heated by a 5"×1" ceramic band heater clamped to the outside of the reactor. A thermocouple, positioned between the reactor wall and the heater measured the reactor temperature.

At a temperature of 400° C., 10 sccm ($1.7 \times 10^{-7}$ $m^3/s$) of nitrogen and 15 sccm ($2.5 \times 10^{-7}$ $m^3/s$) of HFC-245cb ($CF_3CF_2CH_3$) were mixed and flowed through the reactor giving a contact time of 60 seconds. The flows were then reduced to 5 sccm of nitrogen ($8.3 \times 10^{-8}$ $m^3/s$) and 7.5 sccm ($1.3 \times 10^{-7}$ $m^3/s$) of HFC-245cb ($CF_3CF_2CH_3$) giving a contact time of 120 seconds. The effluent was sampled under both sets of conditions and analyzed by $^{19}F$ NMR. Additionally, the effluent was analyzed by GC/FID to determine concentrations as listed in Table 2.

TABLE 2

| Temp., | $N_2$ flow | HFC-245cb | Concentrations, (GC area %) | | |
|---|---|---|---|---|---|
| ° C. | (sccm) | flow (sccm) | HFC-1234yf | HFC-245cb | Unknowns |
| 400 | 10 | 15 | 6.0 | 93.9 | 0.1 |
| 400 | 5 | 7.5 | 22.8 | 76.4 | 0.8 |

Example 3

Azeotropic Distillation for the Separation of HFC-1234yf from HF Without an Entrainer Example 3 demonstrates that HF may be separated from HFC-1234yf by azeotropic distillation with no entrainer. Referring now to FIG. 1, a composition comprising HF and HFC-1234yf is fed to a first column 110 via stream 100. This first column contains 8 theoretical stages and is operated under appropriate conditions to approach the low-boiling HF/HFC-1234yf azeotrope. Because HF is being fed to this first column in excess of that needed to form the azeotrope with the HFC-1234yf, HF is recovered as a product stream out the bottoms of the column via stream 120, while a composition near to the HF/HFC-1234yf azeotrope is recovered as distillate via stream 130. Stream 130 is condensed in 140, mixed with the nearly azeotropic composition recycled from the second column via stream 250 and the combined stream is sub-cooled in cooler 160 and sent to decanter 180 where the combined stream 170 separates into separate HF-rich 190 and HFC-1234yf-rich 200 streams. Stream 190 is recycled to the first column as reflux. Stream 200 is fed to the top stage of a second distillation column 210, containing 19 theoretical stages and operated under conditions to approach the HF/HFC-1234yf azeotrope. Because HFC-1234yf is being fed to this second column in excess of that needed to form the low-boiling HF/HFC-1234yf azeotrope, HFC-1234yf is recovered as a product stream out the bottoms of the column via stream 220 while a composition close to the HF/HFC-1234yf azeotrope is recovered as distillate via stream 230. Stream 230 is condensed in 240, mixed with the nearly azeotropic composition from the first column via stream 150 and fed to cooler 160 and then decanter 180.

The data in Table 3 were calculated using measured and calculated thermodynamic properties.

theoretical stages via stream 100. An HF-rich and propane-lean composition is also fed to the top stage of column 110 via stream 190. Because the combined amount of HF in streams 100 and 190 is in excess of that needed to form the low-boiling HF/HFC-1234yf azeotrope, HF is recovered as a product stream essentially free of both HFC-1234yf and propane from the bottom of column 110 via stream 120. A composition enriched in HFC-1234yf relative to the combined streams 100 & 190 and preferably near the HF/HFC-1234yf azeotrope is recovered as the distillate via stream 130. Stream 130 is condensed by condenser 140 forming stream 150 and then mixed with both the condensed distillate stream 250 from a second distillation column and, as needed, additional propane added via stream 260. Combined streams 150, 250, and 260 are sent to cooler 160 and then to decanter 180 where the sub-cooled liquid stream 170 separates into HF-rich and HF-lean or organic-rich liquid phase fractions which are removed via streams 190 and 200, respectively. The HFC-1234yf present in the decanter primarily distributes into the propane-rich liquid phase fraction. Stream 190 is recycled to the top of the first column. The HF-lean liquid phase fraction in the decanter is fed to the top stage of a second distillation column 210, which contains 25 theoretical stages, via stream 200. Because the amount of HFC-1234yf in stream 200 is in excess of that needed to form the low-boiling propane/HFC-1234yf, HFC-1234yf/HF, and propane/HFC-1234yf/HF azeotropes, i.e., the composition of stream 200 lies in the

TABLE 3

| Component or variable | First dist. col. feed | First column distillate | First dist. col. bottom (HF product) | HF rich phase (from decanter) | HFC-1234yf rich phase (from decanter) | Second distillate | Second dist. col. Bottom (HFC-1234yf product) |
|---|---|---|---|---|---|---|---|
| Stream No. | 100 | 130 | 120 | 190 | 200 | 230 | 220 |
| HF, wt % | 14.9 | 12.3 | 100 | 45.8 | 2.5 | 4.3 | 1 ppm |
| HFC-1234yf, wt % | 85.1 | 87.7 | 10 ppm | 54.2 | 97.5 | 95.7 | 100 |
| Temp, °C. | 30.0 | 47.5 | 102. | −40.0 | −40.0 | 39.7 | 43.2 |
| Pres, psia | 165 | 160 | 160 | 159 | 159 | 160 | 160 |

Example 4

Azeotropic Distillation for the Separation of HFC-1234yf from HF Using Propane as the Entrainer Example 4 demonstrates that HF may be separated from HFC-1234yf by azeotropic distillation using propane as the entrainer. This ternary mixture forms three minimum-boiling binary azeotropes and a minimum-boiling ternary azeotrope.

Referring now to FIG. 2, a composition consisting of HF and HFC-1234yf is fed to a first column 110 containing 9 distillation region bounded by these three azeotrope compositions and pure HFC-1234yf, HFC-1234yf is recovered as a product stream essentially free of both HF and propane from the bottom of column 210 via stream 220. A ternary composition enriched in propane relative to stream 200 and in the same distillation region leaves the top of the second column as the distillate via stream 230. Stream 230 is condensed by condenser 240, forming stream 250, and combined with streams 150 and 260 as previously described.

The data in Table 4 were calculated using measured and calculated thermodynamic properties

TABLE 4

| Component or variable | First dist. col. feed | First distillate | First dist. col. bottom (HF product) | HF rich phase (from decanter) | Propane rich phase (from decanter) | Second distillate | Second dist. col. Bottom (HFC-1234yf product) |
|---|---|---|---|---|---|---|---|
| Stream No. | 100 | 130 | 120 | 190 | 200 | 230 | 220 |
| HF, wt % | 14.9 | 7.8 | 100 | 46.0 | 1.0 | 1.5 | <1 ppm |
| HFC-1234yf, wt % | 85.1 | 91.9 | 1 ppm | 52.3 | 79.2 | 68.6 | 100 |
| Propane, wt % | 0 | 0.3 | <1 ppm | 1.7 | 19.8 | 29.9 | 1 ppm |
| Temp, °C. | 25.0 | 26.3 | 88.6 | −20.0 | −20.0 | 15.3 | 15.3 |
| Pres, psia | 165 | 115 | 115 | 115 | 115 | 115 | 115 |

Example 5

Azeotropic Distillation for the Separation of HFC-1234yf from HF Using CFC-115 as the Entrainer Example 5 demonstrates that HF may be separated from HFC-1234yf by azeotropic distillation using CFC-115 as an entrainer.

Referring now to FIG. 2, a composition consisting of HF and HFC-1234yf is fed to a first column 110 containing 9 theoretical stages via stream 100. An HF-rich and CFC-115-lean composition is also fed to the top stage of column 110 via stream 190. Because the combined amount of HF in streams 100 and 190 is in excess of that needed to form the low-boiling HF/HFC-1234yf azeotrope, HF is recovered as a product stream essentially free of both HFC-1234yf and CFC-115 from the bottom of column 110 via stream 120. A composition enriched in HFC-1234yf relative to the combined streams 100 & 190 and preferably near the HF/HFC-1234yf azeotrope is recovered as the distillate via stream 130. Stream 130 is condensed by condenser 140 forming stream 150 and then mixed with both the condensed distillate stream 250 from a second distillation column and, as needed, additional CFC-115 added via stream 260. Combined streams 150, 250, and 260 are sent to cooler 160 and then to decanter 180 where the sub-cooled liquid stream 170 separates into HF-rich and HF-lean or organic-rich liquid phase fractions which are removed via streams 190 and 200, respectively. The HFC-1234yf present in the decanter primarily distributes into the CFC-115-rich liquid phase fraction. Stream 190 is recycled to the top of the first column. The HF-lean liquid phase fraction in the decanter is fed to the top stage of a second distillation column 210, which contains 25 theoretical stages, via stream 200. Because the amount of HFC-1234yf in stream 200 is in excess of that needed to form the low-boiling HFC-1234yf/HF, CFC-115/HFC-1234yf, and CFC-115/HFC-1234yf/HF azeotropes, i.e., the composition of stream 200 lies in the distillation region bounded by these three azeotrope compositions and pure HFC-1234yf, HFC-1234yf is recovered as a product stream essentially free of both HF and CFC-115 from the bottom of column 210 via stream 220. A ternary composition enriched in CFC-115 relative to stream 200 and in the same distillation region leaves the top of the second column as the distillate via stream 230. Stream 230 is condensed by condenser 240, forming stream 250, and combined with streams 150 and 260 as previously described.

The data in Table 5 were calculated using measured and calculated thermodynamic properties entrainer. One possible source for such a mixture is in an HFC-245eb and/or HFC-245cb dehydrofluorination process operated with partial conversion, that is, the mixture contains equimolar amounts of HF and the HFC-1234yf.

Referring now to FIG. 6, a stream comprising HF, HFC-1234yf, and at least one of HFC-245cb and HFC-245eb is fed to the 25th stage from the top of a first distillation column 20 containing 40 theoretical stages via stream 10. The HFC-245eb and/or HFC-245cb present are separated from HF and HFC-1234yf by azeotropic distillation in this first distillation column 20 using the HFC-1234yf in the feed mixture as the entrainer. However, the equimolar HF/HFC-1234yf mixture from a dehydrofluorination process does not contain enough HFC-1234yf to cause all of the HF to distill overhead. Consequently, supplemental HFC-1234yf in an amount sufficient to cause all of the HF to distill away from the HFC-245eb and/or HFC-245cb is added via a second, HFC-1234yf-enriched stream 95 that is added as reflux to the top of the first column 20. Column 20 is operated under conditions to approach the low-boiling HF/HFC-1234yf azeotrope, which is removed as distillate via stream 40. An essentially HF-free mixture comprising HFC-245eb and/or HFC-245cb is removed from the bottom of the column via stream 30 and may, if desired, be returned to the dehydrofluorination reaction step. Distillate stream 40 is condensed and cooled in a first condenser 50 and a first cooler 60, and then sent to first decanter 70 operated such that the distillate separates into HF-rich and HFC-1234yf-rich liquid phase fractions in the decanter, which are removed via streams 80 and 90, respectively. Part of the HFC-1234yf-rich stream 90 is returned to the first column as reflux and as the source of supplemental HFC-1234yf previously described via stream 95 and the remaining portion is fed to a second distillation column 110 via stream 100 where it is separated into an HFC-1234yf bottoms product, removed via stream 120, that is essentially free of HF and a distillate composition near to the HF/HFC-1234yf azeotrope, removed via stream 130. Because the reflux stream 95 is enriched in HFC-1234yf relative to the HFC-1234yf/HF azeotropic composition, the reflux stream 95 supplies the additional HFC-1234yf needed to make the HFC-245eb and/or HFC-245cb bottoms product from the first column, removed via stream 30, essentially free of HF, thereby reducing the amount of purified HFC-1234yf that must be recycled from the second column to the first column. As shown in FIG. 6, at sufficiently high reflux flows, the need for recycling any of the purified HFC-1234yf from the bottom of the second column to the first column can be completely eliminated. The first decanter's HF-rich phase fraction is fed to a third distillation column 210 via stream 80. Both feeds

TABLE 5

| Component or variable | First dist. col. feed | First distillate | First dist. col. bottom (HF product) | HF rich phase (from decanter) | CFC-115 rich phase (from decanter) | Second distillate | Second dist. col. Bottom (HFC-1234yf product) |
|---|---|---|---|---|---|---|---|
| Stream No. | 100 | 130 | 120 | 190 | 200 | 230 | 220 |
| HF, wt % | 14.9 | 7.7 | 100 | 29.7 | 3.3 | 3.5 | <1 ppm |
| HFC-1234yf, wt % | 85.1 | 90.3 | 1 ppm | 62.5 | 78.6 | 76.9 | 100 |
| CFC-115, wt % | 0 | 2.0 | <1 ppm | 7.8 | 18.1 | 19.6 | 10 ppm |
| Temp, ° C. | 25.0 | 26.3 | 88.6 | −20.0 | −20.0 | 25.0 | 30.5 |
| Pres, psia | 165 | 115 | 115 | 115 | 115 | 115 | 115 |

Example 6

This example shows how HF, HFC-1234yf, HFC-245eb and/or HFC-245cb may be separated using HFC-1234yf as an (streams 80 and 200) to the third column have compositions containing excess HF relative to the HF/HFC-1234yf azeotrope so that an HF bottoms product essentially free of HFC-1234yf may be obtained in column 210 and removed via stream 220. The distillate from the third column has a composition near to the HF/HFC-1234yf azeotrope and is removed via stream 230. As in earlier examples, the distillates (streams 130 and 230) from columns 110 and 210 are condensed in condensers 140 and 240, forming streams 150 and 250, respectively, mixed together, and sent first to a second cooler 160 and then to a second decanter 180 where separate HFC-1234yf-rich and HF-rich liquid phase fractions are formed. The HFC-1234yf-rich fraction is removed from decanter 180 via stream 190 and fed to the second column 110 for further separation. The HF-rich fraction is removed from decanter 180 via stream 200 and fed to the third column 210 for further separation.

The data in Table 6 were obtained by calculation using measured and calculated thermodynamic properties.

TABLE 6

| Component or variable | Feed | First btm | First Dist | First HF-rich phase | First 1234yf-rich phase | Sec. Btm | Second Dist | Third btms | Third dist |
|---|---|---|---|---|---|---|---|---|---|
| Stream # | 10 | 30 | 40 | 80 | 90 | 120 | 130 | 220 | 230 |
| HF, wt % | 5.0 | <1 ppm | 2.9 | 45.8 | 2.5 | 1 ppm | 5.7 | 100 | 7.6 |
| HFC-245eb, wt % | 66.7 | 100 | 1 ppm | <1 ppm | 1 ppm | <1 ppm | <1 ppm | <1 ppm | <1 ppm |
| HFC-1234yf, wt % | 28.3 | <1 ppm | 97.1 | 54.2 | 97.5 | 100 | 94.3 | 1 ppm | 92.4 |
| Temp, °C. | 37.0 | 61.4 | 3.7 | −40.0 | −40.0 | 5.6 | 2.8 | 60.7 | 3.3 |
| Pres, psia | 55.2 | 55.4 | 54.7 | 54.7 | 54.7 | 54.8 | 54.7 | 54.8 | 54.7 |

Example 7

This example shows how HFC-245eb that forms an azeotrope with HF and HFC-1234yf that is partially miscible with and forms an azeotrope with HF can both be separated from a mixture comprising HF, HFC-245eb and HFC-1234yf by azeotropic distillation using n-propane as an added entrainer.

Referring now to FIG. 7, the first distillation column 20, condenser 50, cooler 60, and decanter 70 in this embodiment operates identically to the similarly numbered equipment in Example 6 as just described. The HF-rich and part of the HFC-1234yf-rich liquid distillate fractions from the first column's decanter 70 are fed via streams 80 and 100 to distillation columns 210 and 110 which recover purified HF and HFC-1234yf, respectively.

The data in Table 7 were obtained by calculation using measured and calculated thermodynamic properties.

Example 8

This Example shows one way in which HF may be separated from HFC-1234yf and HFC-245eb and/or HFC-245cb. The composition of the feed mixture in this example is such as one might obtain from a dehydrofluorination reactor operated with partial conversion, i.e., it contains equimolar amounts of HF and HFC-1234yf.

Referring now to FIG. 4, a stream comprising HF, HFC-1234yf, and HFC-245cb is fed to a first distillation column 110 via stream 100. An entrainer-rich stream is also fed to this column via stream 190. In this example, CFC-115 is used as the entrainer.

Column 110 contains 34 theoretical stages and is operated under conditions to cause HF to distill overhead with the entrainer due to the influence of the low-boiling HF/CFC-115 azeotrope. Sufficient CFC-115 is fed to this first column via stream 190 such that HFC-1234yf and HFC-245cb may be obtained essentially free of CFC-115 and HF as the bottoms from column 110 via stream 120. The HFC-1234yf and HFC-245cb in stream 120 may then optionally be separated from each other by conventional distillation and the HFC-245cb optionally recycled back to a dehydrofluorination reactor to form HFC-1234yf. The distillate from column 110, removed via stream 130, contains essentially all of the CFC-115 and HF in column feeds 100 and 190 and, optionally, some HFC-245cb and/or HFC-1234yf. This first distillate stream 130 is condensed by condenser 140 to form stream 150, which is then mixed with condensed distillate stream 250 from the second distillation column and, as needed, additional fresh CFC-115 added via stream 260. This combined stream is sub-cooled by cooler 160 and sent via stream 170 to decanter

TABLE 7

| Component or variable | Feed (10) | First btm (30) | First Dist (40) | First HF-rich phase (80) | First 1234yf-rich phase (90) | Sec. Btm (120) | Second Dist (130) | Third btms (220) | Third dist (230) |
|---|---|---|---|---|---|---|---|---|---|
| HF, wt % | 4.9 | <1 ppm | 2.9 | 45.8 | 2.5 | 1 ppm | 1.3 | 100 | 7.6 |
| HFC-245eb, wt % | 66.7 | 100 | 1 ppm | <1 ppm | 1 ppm | <1 ppm | <1 ppm | <1 ppm | <1 ppm |
| HFC-1234yf, wt % | 28.4 | <1 ppm | 97.1 | 54.2 | 97.5 | 8.1 | 17.0 | <1 ppm | 92.1 |
| Propane, wt % | 0 | 0 | 0 | 0 | 0 | 91.9 | 81.7 | <1 ppm | 0.3 |
| Temp, °C. | 37.0 | 61.4 | 3.7 | −40.0 | −40.0 | −8.1 | −9.1 | 60.7 | 3.2 |
| Pres, psia | 55.2 | 55.4 | 54.7 | 54.7 | 54.7 | 54.7 | 54.8 | 54.8 | 54.7 |

Figure 8:
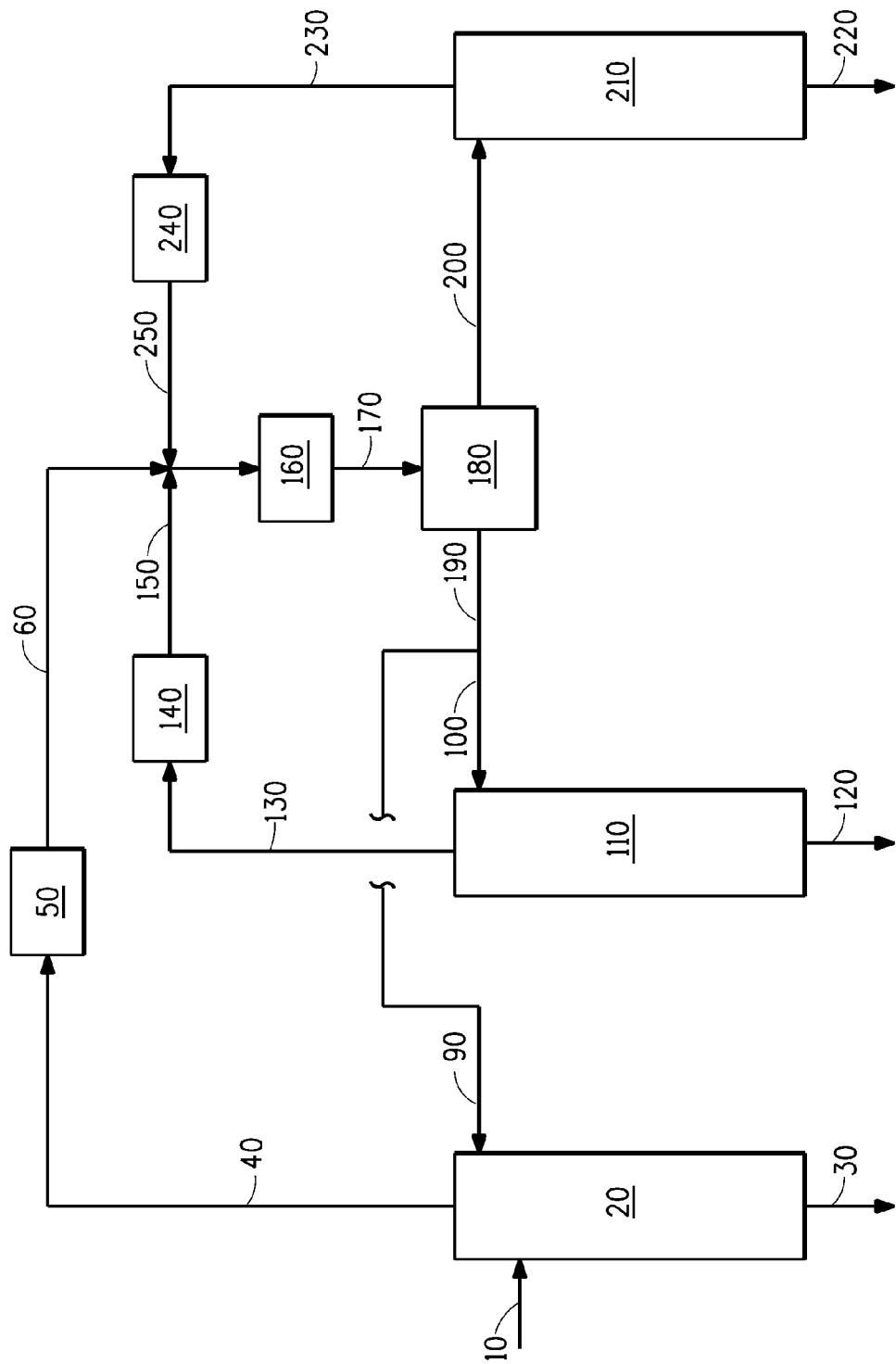
FIG. 8 illustrates another embodiment of the process shown in FIG. 6, wherein the three columns, 20, 110, and 220, share one decanter.

In other embodiments of the invention, (a) condensers 140 and 240 may be combined into a single unit, (b) coolers 60 and 160 can be combined into a single unit and decanters 70 and 180 can be combined into a unit, as shown in FIG. 8, or (c) the three condensers 50, 140 & 240 can be combined into a single unit, coolers 60 and 160 can be combined into a single unit, and decanters 70 and 180 can be combined into a unit.

180 where it separates into separate entrainer-rich and HF-rich liquid fractions which are removed via streams 190 and 200, respectively. The majority of the HFC-245cb and HFC-1234yf present in the decanter partition into the CFC-115-rich phase fraction that is fed to the first distillation column 110 via stream 190. The HF-rich fraction from the decanter is fed via stream 200 to a second distillation column 210 con taining 8 theoretical stages and operated under conditions such that a bottoms stream of HF essentially free of HFC-245cb, HFC-1234yf, and CFC-115 is produced and removed via stream 220. The distillate from column 210, removed via stream 230 and containing essentially all of the HFC-245cb, HFC-1234yf, and CFC-115 present in the column feed (stream 200) plus the HF not recovered in product stream 220, is condensed by condenser 240 and removed via stream 250. Condensed distillate stream 250 is combined with both the condensed distillate stream 150 from the first column and, as needed, fresh entrainer, added via stream 260, then cooled and fed to the decanter for further separation.

The data in Table 8 were obtained by calculation using measured and calculated thermodynamic properties.

TABLE 8

| Component or variable | Feed | First col btm | First Dist | Entrainer-rich phase | HF-rich phase | Second col btm | Second Dist |
|---|---|---|---|---|---|---|---|
| Stream # | 100 | 120 | 130 | 190 | 200 | 220 | 230 |
| HF, wt % | 6.4 | <1 ppm | 4.1 | 0.9 | 58.9 | 100 | 50.1 |
| CFC-115, wt % | 0 | 1 ppm | 56.7 | 58.5 | 16.4 | <1 ppm | 19.9 |
| HFC-245cb, wt % | 57.1 | 61.0 | 23.5 | 0.2 | 12.3 | <1 ppm | 15.0 |
| HFC-1234yf, wt % | 36.5 | 39.0 | 15.7 | 16.2 | 12.4 | <1 ppm | 15.0 |
| Temp, °C. | 30.0 | 38.3 | 19.0 | −35.0 | −35.0 | 88.9 | 76.1 |
| Pres, psia | 165 | 116 | 115 | 115 | 115 | 116 | 115 |

Example 9

Azeotropic Distillation for the Separation of HFC-1234yf from HF Using PFC-218 as the Entrainer Example 9 demonstrates that HF may be separated from HFC-1234yf by azeotropic distillation using PFC-218 as an entrainer. Referring now to FIG. 2, a composition consisting of HF and HFC-1234yf is fed to a first column 110 containing 9 theoretical stages via stream 100. An HF-rich and PFC-218-lean composition is also fed to the top stage of column 110 via stream 190. Because the combined amount of HF in streams 100 and 190 is in excess of that needed to form the low-boiling HF/HFC-1234yf azeotrope, HF is recovered as a product stream essentially free of both HFC-1234yf and PFC-218 from the bottom of column 110 via stream 120. A composition enriched in HFC-1234yf relative to the combined streams 100 & 190 and preferably near the HF/HFC-1234yf azeotrope is recovered as the distillate via stream 130. Stream 130 is condensed by condenser 140 forming stream 150 and then mixed with both the condensed distillate stream 250 from a second distillation column and, as needed, additional PFC-218 added via stream 260. Combined streams 150, 250, and 260 are sent to cooler 160 and then to decanter 180 where the sub-cooled liquid stream 170 separates into HF-rich and HF-lean or organic-rich liquid phase fractions which are removed via streams 190 and 200, respectively. The HFC-1234yf present in the decanter primarily distributes into the PFC-218-rich liquid phase fraction. Stream 190 is recycled to the top of the first column. The HF-lean liquid phase fraction in the decanter is fed to the top stage of a second distillation column 210, which contains 25 theoretical stages, via stream 200. HFC-1234yf is recovered as a product stream essentially free of both HF and PFC-218 from the bottom of column 210 via stream 220. A ternary composition enriched in PFC-218 relative to stream 200 leaves the top of the second column as the distillate via stream 230.

A ternary composition enriched in PFC-218 relative to stream 200 and in the same distillation region leaves the top of the second column as the distillate via stream 230. Stream 230 is condensed by condenser 240, forming stream 250, and combined with streams 150 and 260 as previously described.

The data in Table 9 were calculated using measured and calculated thermodynamic properties

TABLE 9

| Component or variable | First dist. col. feed | First distillate | First dist. col. bottom (HF product) | HF rich phase (from decanter) | PFC-218 rich phase (from decanter) | Second distillate | Second dist. col. Bottom (HFC-1234yf product) |
|---|---|---|---|---|---|---|---|
| Stream No. | 100 | 130 | 120 | 190 | 200 | 230 | 220 |
| HF, wt % | 14.9 | 7.6 | 100.0 | 23.7 | 3.5 | 3.6 | <1 ppm |
| HFC-1234yf, wt % | 85.1 | 89.7 | 1 ppm | 68.1 | 77.1 | 76.4 | 100.0% |
| PFC-218, wt % | 0.0 | 2.7 | <1 ppm | 8.2 | 19.3 | 20.0 | 10 ppm |
| Temp, °C. | 25.0 | 26.2 | 88.6 | −10.0 | −10.0 | 25.2 | 30.5 |
| Pres, psia | 164.7 | 114.7 | 114.7 | 114.7 | 114.7 | 114.7 | 114.8 |

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments.

However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any sub combination. Further, references to values stated in ranges include each and every value within that range.

What is claimed is:

1. A process for separating a mixture comprising HF and HFC-1234yf, said process comprising:
    a. feeding the mixture comprising HF and HFC-1234yf to a first distillation column;
    b. removing an azeotrope composition comprising HF and HFC-1234yf as a first distillate and either i) HF or ii) HFC-1234yf as a first column bottoms composition;
    c. decanting the first distillate to form 2 liquid phases, being i) an HF-rich phase and ii) an HFC-1234yf-rich phase; and
    d. recycling a first liquid phase enriched in the same compound that is removed as the first column bottoms, said first liquid phase being either i) HF-rich phase or ii) HFC-1234yf-rich phase, back to the first distillation column;
        wherein the first distillation column is operated at a pressure of from about 14.7 psia (101 kPa) to about 300 psia (2068 kPa), with a top temperature of from about −50° C. to about 200° C. and a bottom temperature from about −30° C. to about 220° C.

2. The process of claim 1, further comprising feeding a second liquid phase not recycled in step (d), said second liquid phase being either i) HF-rich phase or ii) HFC-1234yf-rich phase, to a second distillation column.

3. The process of claim 1, wherein said HFC-1234yf in the mixture is present in a concentration greater than the azeotrope composition for hydrogen fluoride and said HFC-1234yf, and wherein the first column bottoms composition is HFC-1234yf that is essentially free of hydrogen fluoride, and wherein said first liquid phase is enriched in HFC-1234yf.

4. The process of claim 3, further comprising:
    i. feeding the hydrogen fluoride-rich phase from the decanter to a second distillation column;
    ii. recovering hydrogen fluoride essentially free of HFC-1234yf from the bottom of the second distillation column; and
    iii. recycling a second distillate composition to the two liquid phases in the decanter.

5. The process of claim 1, wherein hydrogen fluoride is present in a concentration greater than the azeotrope concentration for hydrogen fluoride and said HFC-1234yf, and wherein the first column bottoms composition is hydrogen fluoride essentially free of HFC-1234yf, and wherein said first liquid phase is enriched in hydrogen fluoride.

6. The process of claim 5 further comprising:
    i. feeding the HFC-1234yf-rich phase from the decanter to a second distillation column;
    ii. recovering HFC-1234yf essentially free of hydrogen fluoride from the bottom of the second distillation column; and
    iii. recycling a second distillate composition to the two liquid phases in the decanter.

7. A process for the purification of an HFC-1234yf from a mixture comprising HFC-1234yf and HF, said process comprising:
    a. adding an entrainer to the mixture comprising HFC-1234yf and HF thus forming a second mixture;
    b. distilling said second mixture in a first distillation step to form a first distillate composition comprising HF, HFC-1234yf, and entrainer, and a first bottoms composition comprising either i) HFC-1234yf, or ii) HF;
    c. condensing said first distillate composition to form two liquid phases, being i) an HF-rich phase and ii) an entrainer-rich phase; and
    d. optionally recycling a first liquid phase back to the first distillation step, wherein said first liquid phase being either i) the HF-rich phase when the first bottoms composition comprises HF or ii) the entrainer-rich phase when the first bottoms composition comprises HFC-1234yf.

8. The process of claim 7, wherein said HFC-1234yf is present in said mixture in a concentration greater than the azeotrope concentration for said HFC-1234yf and HF; and wherein said first bottoms composition comprises HFC-1234yf; said process further comprising feeding the entrainer-rich phase to a second distillation step and forming a second distillate composition comprising entrainer, HFC-1234yf and HF and a bottoms composition comprising HF essentially free of entrainer.

9. The process of claim 7, wherein said HF is present in said mixture in a concentration greater than the azeotrope concentration for said HFC-1234yf and HF; and wherein said first bottoms composition comprises HF; said process further comprising feeding the HF-rich phase to a second distillation step and forming a second distillate composition comprising entrainer, HFC-1234yf and HF and a bottoms composition comprising entrainer essentially free of HF.

10. The process of claim 8 or 9, further comprising recycling said second distillate composition back to the two liquid phases.

11. A process for the separation of HFC-1234yf from a mixture of HFC-1234yf, HF, and at least one of HFC-245cb or HFC-245eb, said process comprising:
    a. subjecting said mixture to a first distillation step, wherein additional HFC-1234yf is fed from a second distillation step, to form a first distillate comprising an azeotrope of HFC-1234yf and HF and a first bottoms composition comprising at least one of HFC-245cb or HFC-245eb;
    b. feeding said first distillate to a second distillation step to form a second distillate comprising an azeotrope of HFC-1234yf and HF and a second bottoms composition comprising HFC-1234yf essentially free of HF;
    c. decanting said second distillate to form two liquid phases, being i) an HF-rich phase and ii) an HFC-1234yf-rich phase; and
    d. recycling the HFC-1234yf-rich phase from (c) back to the first distillation step.

12. The process of claim 11 further comprising feeding the HF-rich phase to a third distillation step to form a third distillate comprising an azeotrope of HFC-1234yf and HF and a third bottoms composition comprising HF essentially free of HFC-1234yf.

13. A process for separating HF from a mixture comprising HFC-1234yf, HF, and at least one of HFC-245cb or HFC-245eb, said process comprising:
    a. adding an entrainer to the mixture comprising HFC-1234yf, HF, and at least one of HFC-245cb or HFC-245eb thus forming a second mixture;

b. distilling said second mixture in a first distillation step to form a first distillate composition comprising HF and entrainer and a first bottoms composition comprising HFC-1234yf and at least one of HFC-245cb or HFC-245eb;
c. condensing said first distillate composition to form two liquid phases, being (i) an entrainer-rich phase and (ii) an HF-rich phase; and
d. recycling the entrainer-rich phase back to the first distillation step.

14. The process of claim 13 further comprising feeding the HF-rich phase to a second distillation step and forming a second distillate composition comprising an azeotrope of entrainer and HF and a second bottoms composition comprising HF essentially free of entrainer.

15. The process of claim 14 further comprising recycling said second distillate composition back to the two liquid phases.

16. The process of claim 7 or 13, wherein said entrainer is selected from the group consisting of hydrocarbons, chlorocarbons, chlorofluorocarbons, hydrochlorofluorocarbons, hydrofluorocarbons, perfluorocarbons, fluoroethers, HFPO, $SF_6$, chlorine, hexafluoroacetone, and mixtures thereof.

* * * * *